US006992202B1

(12) United States Patent
Banger et al.

(10) Patent No.: US 6,992,202 B1
(45) Date of Patent: Jan. 31, 2006

(54) SINGLE-SOURCE PRECURSORS FOR TERNARY CHALCOPYRITE MATERIALS, AND METHODS OF MAKING AND USING THE SAME

(75) Inventors: Kulbinder K. Banger, Lakewood, OH (US); Aloysius F. Hepp, Bay Village, OH (US); Jerry D. Harris, Nampa, ID (US); Michael Hyun-Chul Jin, Akron, OH (US); Stephanie L. Castro, Westlake, OH (US)

(73) Assignees: Ohio Aerospace Institute, Cleveland, OH (US); The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 83 days.

(21) Appl. No.: 10/698,118

(22) Filed: Oct. 31, 2003

Related U.S. Application Data

(60) Provisional application No. 60/422,904, filed on Oct. 31, 2002, provisional application No. 60/443,117, filed on Jan. 28, 2003.

(51) Int. Cl.
*C07F 19/00* (2006.01)
*C23C 16/00* (2006.01)
*C30B 23/00* (2006.01)

(52) U.S. Cl. ............................ 556/28; 556/21; 556/30; 556/31; 427/248.1; 427/587; 427/593; 117/3; 117/84

(58) Field of Classification Search .................. 556/21, 556/28, 30, 31; 427/587, 593, 248.1; 117/3, 117/84
See application file for complete search history.

(56) References Cited

OTHER PUBLICATIONS

Chhipa et al., Indian Journal of Chemistry, vol. 28A, No. 5, pp 396-399 (May 1989).*
Applied Organometallic Chemistry Homepage, vol. 16, No. 11, Wiley-Interscience (Nov. 29, 2004).*
Contreas, M., et al., "Progress Toward 20% Efficiency in Cu(In,Ga)Se2 Polycrystalline Thin-Film Solar Cells", *Prog. Photovolt. Res. App.,* 1999, 7, pp. 311-316.
Hoffman, D., et al., "Thin-Film Solar Array Earth-Orbit Mission Applicability Assessment", *XVII Space Photovoltaic Research and Tech. Conf.,* 2001.
Bailey, S.G., et al., "Space Photovoltaics", *Prog. Photovolt. Res. App.,* 1998, 6, 1-14.
Schock, H.W., et al., "Development of CIS Solar Cells for Space Applications", Eds. Schmid, J., et al., $2^{th}$ *World Photovolt. Solar Energy Conf.,* Vienna, 1998, pp. 1-4.
Tarrant, D., et al., "I-III-VI$_2$ Multinary Solar Cells Based on CuInSe$_2$", *Proc. $23^{rd}$ IEEE Photovoltaic Specialist Conference,* 1993, ABSTRACT.

(Continued)

*Primary Examiner*—Porfirio Nazario-Gonzalez
(74) *Attorney, Agent, or Firm*—Pearne & Gordon LLP

(57) ABSTRACT

A single source precursor for depositing ternary I-III-VI$_2$ chalcopyrite materials useful as semiconductors. The single source precursor has the I-III-VI$_2$ stoichiometry "built into" a single precursor molecular structure which degrades on heating or pyrolysis to yield the desired I-III-VI$_2$ ternary chalcopyrite. The single source precursors effectively degrade to yield the ternary chalcopyrite at low temperature, e.g. below 500° C., and are useful to deposit thin film ternary chalcopyrite layers via a spray CVD technique. The ternary single source precursors according to the invention can be used to provide nanocrystallite structures useful as quantum dots. A method of making the ternary single source precursors is also provided.

59 Claims, 16 Drawing Sheets

OTHER PUBLICATIONS

Basol, B.M., et al., "Cu(In,Ga)Se$_2$ Thin Films and Solar Cells Prepared by Selenization of Metallic Precursors", *J. of Vacuum Science and Technology A*, 1996, 14A, pp. 2251-2256.

Probst, V., et al., "Rapid CIS-Process for High Efficiency PV-Modules: Development Towards Large Area Processing", *Thin Solid Films*, 2001, 387, pp. 262-267.

Dimmler, B., et al., "Scalability and Pilot Operation in Solar Cells of CuInSe$_2$ and Their Alloys", *Prog. Photovolt. Res. Appl.*, 1998, 6, pp. 193-199.

Park, S.C., et al., "Fabrication of CuInSe$_2$ Films and Solar Cells by the Sequential Evaporation of In$_2$Se$_3$ and Cu$_2$Se Binary Compounds", *Sol. Energy Mater. Sol. Cells*, 2001, 69, pp. 99-105.

Guillen, C., et al. "Recrystallization and Components Redistribution Processes in Electrodeposited CuInSe$_2$ Thin Films", *Thin Solid Films*, 2001, 387, pp. 57-59.

Eberspacher, C., et al., "Thin-Film CIS Alloy PV Materials Fabricated Using Non-Vacuum, Particles-Based Techniques", *Thin Solid Films*, 2001, 387, pp. 18-22.

Klenk, M., et al., "Properties of Flash Evaporated Chalcopyrite Absorber Films and Solar Cells", *Thin Solid Films*, 2001, 387, pp. 47-49.

Dzionk, C., et al., "Phase Formation During the Reactive Annealing of Cu-In Films in H$_2$S Atmosphere", *Thin Solid Films*, 1997, 299, pp. 38-44.

Krunks, M., et al., "Composition and Structure of CuInS$_2$ Films Prepared by Spray Pyrolysis", *Thin Solid Films*, 2000, 361-2, pp. 61-64.

Artaud, M.C., et al., "CuInSe$_2$ Thin Films Grown by MOCVD: Characterization, First Devices", *Thin Solid Films*, 1998, 324, pp. 115-123.

Jones, A.C., et al., "CVD of Compound Semiconductors: Precursors Synthesis, Development & Application", *VCH Press*, 1997, pp. 42-99.

Nomura, R., et al., "Preparation of Copper-Indium-Sulfide Thin Films by Solution Pyrolysis of Organometallic Sources", *Chem. Let.*, 1988, pp. 1849-1850.

Nomura, R., et al., "Oxygen-or Sulphur-Containing Organoindium Compounds for Precursors of Indium Oxide and Sulphide Thin Films", *Polyhedron*, 1990, 9, pp. 361-366.

Nomura, R., et al., "Preparation of CuInS$_2$ Thin Films by Single-Source MOCVD Process Using Bu$_2$In(SPr)Cu(S$_2$CNPri$_2$)", *J. Mater. Chem.*, 1992, pp. 765-766.

Nomura, R., et al., "Preparation of CuIn$_5$S$_8$ Thin Films by Single-Source Organometallic Chemical Vapour Deposition", *Thin Solid Films*, 1992, 209, pp. 145-147.

Hirpo, W., et al., Synthesis of Mixed Copper-Indium Chalcogenolates. Single Source Precursors for the Photovoltaic Material CuInQ$_2$ (Q =S, Se), *J. Am. Chem. Soc.*, 1993, 115, pp. 1597-1599.

Hollingsworth, J.A., et al., "Spray CVD of Copper Indium Disulfide Films: Control of Microstructure and Crystallographic Orientation", *Chem. Vap. Deposition*, 1999, 5, pp. 105-108.

Hollingsworth, J.A., et al., "Spray Chemical Vapor Deposition of CuInS$_2$ Thin Films for Application in Solar Cell Devices", *Mat. Res. Soc. Symp. Proc.*, 1998, 495, ABSTRACT.

Harris, J.D., et al., "Using Single Source Precursors and Spray Chemical Vapor Deposition to Grow Thin-Film CuInS$_2$", *Proc. of the 28$^{th}$ IEEE Photovoltaic Specialists Conference*, 2000, ABSTRACT.

Banger, Kulbinder K., et al., "Synthesis and Characterization of the First Liquid Single-Source Precursors for the Deposition of Ternary Chalcopyrite (CuInS$_2$) Thin Film Materials", *Chem. Mater.*, 2001, 13(11), pp. 3827-3829.

Hollingsworth, J.A., "Chemical Routes to Nanocrystalline and Thin-Film III-VI and I-III-VI Semiconductors", Dissortation, Washington University, 1999.

Drago, R.S., et al., "E and C Parameters from Hammett Substituent Constants and Use of E and C to Understand Cobalt-Carbon Bond Energies", *Inorg. Chem.*, 1987, 26, pp. 9-14.

Riga, A. et al., "Process Development and Synthesis of CuInSe$_2$ and CuInS$_2$ Precursors of Chemical Vapor Deposition Aided by Thermal Analytical Techniques", *NATAS Annual Conference on Thermal Analysis Applications*, 2001, ABSTRACT.

Hollingsworth, J.A., et al., "Single Source Precursors for Fabrication of I-III-V12 Thin-Film Solar Cells Via Spray CVD", *Thin Solid Films*, 2003 431-432, pp. 63-67.

Banger, K.K., et al., "A Review of Single Source Precursors for the Deposition of Ternary Chalcopyrite Materials", *NASA Conference Publication (2002), 17$^{th}$ Space Photovoltaic Research and Technology Conference*, 2001), pp. 115-125.

Deivaraj, T.C., et al., "Novel Bimetallic Thiocarboxylate Compounds as Single-Source Precursors to Binary and Ternary Metal Sulfide Materials", *Chemistry of Materials*, 2003, 15(12), pp. 2383-2391.

Jin, M. H., et al., "Thin Film Cu1nS2 Prepared by Spray Pyrolysis with Single-Source Precursors", *Conference Record of the IEEE Photovoltaic Specialists Conference*, 2002, 29$^{th}$, ABSTRACT.

Afzaal, M., et al., "New Approach Towards the Deposition of I-III-VI Thin Films", *Materials Research Society Symposium Proceedings*, 2002, pp. 185-190.

Banger, K.K., et al., "Ternary Single-Source Precursors for Polycrystalline Thin-Film Solar Cells", *Applied Organometallic Chemistry*, 2002, 16(11), pp. 617-627.

Banger, K.K., et al., "Facile Modulation of Single Source Precursors: The Synthesis and Characterization of Single Source Precursors for Deposition of Ternary Chalcopyrite Materials", *Thin Solid Films*, 2002, 403-404, 390-395.

Deivaraj, T.C., et al., "Single-Source Precursors to Ternary Silver Indium Sulfide Materials", *Chemical Communications*, 2001, 22, pp. 2304-2305.

Banger, Kulbinder K., et al., "Facile Modulation and Preparation of Single Source Precursors for Low-Temperature Deposition of Ternary Chalcopyrite Materials", *Abstracts of Papers, 222$^{nd}$ ACS National Meeting*, Aug. 26-30, 2001, American Chemical Society, ABSTRACT.

Deivaraj, C.T., et al., "Synthesis and Structure of [(Ph$_3$P)$_2$Ag($\mu$-Cl)($\mu$-SC{O}Ph)In(SC{O}Ph)$_2$]", *Inorganica Chemica Acta*, 336, 2002, pp. 111-114.

Harris, J.D., et al., "Characterization of Cu1nS2 Films Prepared by Atmospheric Pressure Spray Chemical Vapor Deposition", *Materials Science & Engineering*, 2003, B98 (2), pp. 150-155.

Shibata, J., et al., "Transmission Electron Microscopic Studies of LiNb0.5Ta0.5O3 Films Deposited on Sapphire Substrates by Thermal Plasma Spray CVD (Microstructure of LiNb0.5Ta0.5O3 Films Deposited by Thermal Plasma Spray CVD)", *Materials Transactions*, 2002, 43(7), ABSTRACT.

Henderson, D., "Optical and Structural Characterization of Copper Indium Disulfide Thin Films", *Materials & Design*, 2001, 22(7), pp. 585-589.

Vittal, J.J., et al., "Group 11 and 13 Metal Thiocarboxylate Compounds as Single Source Molecular Precursor for Bulk Metal Sulfide Materials and Thin Films", *Progress in Crystal Growth and Characterization of Materials*, 2002, pp. 21-27.

Jin, M.H.C., et al., "The Effect of Film Composition on the Texture and Grain Size of $CuInS_2$ Prepared by Chemical Spray Pyrolysis", *Mat. Res. Soc. Symp. Proc.,* vol. 763, 2003, pp. B8.23.1-B8.23.6.

Tarrant, D., et al., "I-III-$VI_2$ Multinary Solar Cells Based on $CuInSe_2$", *Proc. 23$^{rd}$ IEEE Photovoltaic Specialist Conference*, 1993, pp. 372-378.

Shibata, J., et al., "Transmission Electron Microscopic Studies of $LiNb0.5Ta0.5O3$ Films Deposited on Sapphire Substrates by Thermal Plasma Spray CVD (Microstructure of $LiNb0.5Ta0.5O3$ Films Deposited by Thermal Plasma Spray CVD)", *Materials Transactions*, 2002, 43(7), pp. 1517-1524.

Hollingsworth, J.A., et al., "Spray Chemical Vapor Deposition of $CuInS_2$ Thin Films for Application in Solar Cell Devices", *Mat. Res. Soc. Symp. Proc.,* 1998, vol. 495, pp. 171-176.

Jin, M. H., et al., "Thin Film CuInS2 Prepared by Spray Pyrolysis with Single-Source Precursors", *Conference Record of the 29$^{th}$ IEEE Photovoltaic Specialists Conference*, 2002, pp. 672-675.

Harris, J.D., et al., "Using Single Source Precursors and Spray Chemical Vapor Deposition to Grow Thin-Film $CuInS_2$", *Proc. of the 28$^{th}$ IEEE Photovoltaic Specialists Conference*, 2000, pp. 563-566.

* cited by examiner

SINGLE-SOURCE PRECURSORS FOR TERNARY CHALCOPYRITE MATERIALS, AND METHODS OF MAKING AND USING THE SAME

This application claims the benefit of U.S. Provisional Patent Application Ser. No. 60/422,904 filed Oct. 31, 2002, and U.S. Provisional Patent Application Ser. No. 60/443,117 filed Jan. 28, 2003.

STATEMENT OF GOVERNMENT SPONSORED RESEARCH

The U.S. Government has a paid-up license in this invention and the right in limited circumstances to require the patent owner to license others on reasonable terms as provided for by the terms of Contract Nos. NCC3-947, NCC3-817, NCC3-563, NCC3-958 and NCC3-734, all awarded by the National Aeronautics and Space Administration (Glenn Research Center, Cleveland, Ohio).

This invention was made with Government support under contract Nos. NCC3-947, NCC3-817, NCC3-563, NCC3-958 and NCC3-734, all awarded by the National Aeronautics and Space Administration (Glenn Research Center, Cleveland, Ohio). The Government has certain rights in this invention.

BACKGROUND OF THE INVENTION

The development of thin film flexible lightweight solar cells is of high importance for both terrestrial and space applications. Thin film solar cells use 30–100 times less semiconducting material and are less expensive to manufacture then conventional crystalline silicon cells. Current thin film photovoltaic (PV) research encompasses development of CdTe, Cu(Ga:In)(S:Se)$_2$ (CIS) and thin film silicon based solar cells. One of the most promising technologies lies in the development of polycrystalline thin films, due to their ease of manufacture and importantly, their lightweight structure enables them to achieve higher specific power (W/Kg), than alternative single crystalline devices.

Photovoltaic modules based on ternary chalcopyrite absorber layers, (I-III-VI$_2$; Cu(In:Ga)(S:Se)$_2$) have been the focus of intense investigation. The use of chalcopyrite absorbers are highly appealing since their band gaps correlate well to the maximum photon power density in the solar spectrum for both terrestrial (air mass of 1.5 [AM1.5]), and space applications (AM0), while displaying long term stability and excellent radiation tolerance.

Current methods for depositing ternary crystallite compounds include co-evaporation of multi-source precursors, electrodeposition, reactive-sintering, and flash evaporation, which are often followed by toxic sulphurization/selenization steps at elevated temperatures such as 800° C. Furthermore, under these conditions loss of volatile In/Ga chalcogenides is common. The high temperature requirements of the above methods makes them incompatible with all presently known flexible polyimides, and other polymer substrates. In addition, the use of toxic reagents is a limiting factor.

The use of multi-source inorganic/organometallic precursors in a CVD type process is more appealing due to milder process parameters. However, stoichiometric control of deposited films can be difficult to achieve and film contamination has been reported.

Recently, the synthesis and use of a ternary single source precursor (SSP) having the I-III-VI$_2$ stoichiometry "built in" has been investigated. In 1993, Hirpo and coworkers synthesized [{PPh$_3$}$_2$Cu(SEt)$_2$In(SEt)$_2$], the first known SSP for a ternary I-III-VI$_2$ chalcopyrite material, in this case (CuInS$_2$). Wakgari Hirpo et al., *Synthesis of Mixed Copper-Indium Chalcogenolates. Single-Source Precursors for the Photovoltaic Materials CuInQ$_2$ (Q=S, Se)*, J. Am. Chem. Soc. 1993, 115, 1597–1599. The preparation of hetero binuclear complexes was also reported in the same work. The complexes consisted of tetrahedrally arranged Cu and In centers, with two bridging thiolato and selenolato groups [Eq. 1].

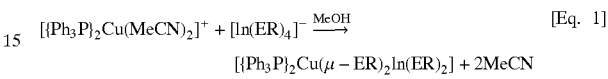

Pyrolysis studies undertaken revealed that the Se derivative could be converted into CuInSe$_2$ at 400–450° C. @ 0.01 mm Hg [Eq.2], but none of the precursors had been evaluated in a thin-film deposition study.

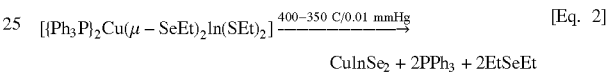

In early studies Nomura et al, reported that an equimolar mixture of [Bu$^i_2$InSPr] and [Cu(S$_2$CNBu$_2$)$_2$] decomposed to afford CuInS$_2$ powders. Nomura, R.; Kanaya, K; Matsuda, H., *Preparation of Copper-Indium-Sulfide thin films by solution Pyrolysis of organometallic sources*, Chem. Let., 1988, 1849–1850. On this basis, solution pyrolysis of this mixture dissolved in ρ-xylene was used to deposit thin-film CuInS$_2$ at 350° C. and low pressure onto glass substrates. Film composition was determined by XRD, which showed broad peaks. XRD revealed the ratios of In/Cu and S/Cu decreased with temperature, and a second phase to be present for films deposited at 350° C. Grain size was estimated to be in the range of 50–100 nm as determined by SEM. It was later realized that the equimolar reaction mixture of [Bu$^i_2$InSPr] and [Cu(S$_2$CNBu$_2$)$_2$] (as used in solution pyrolysis) afforded the single source precursor [Bu$_2$In(SPr$^i$)Cu(S$_2$CNPr$^i_2$)] before decomposing to the chalcopyrite matrix. Analytical and spectral data confirmed that the mixture of [Bu$^i_2$InSPr] and [Cu(S$_2$CNBu$_2$)$_2$] yielded the above SSP. However, the SSP itself was synthesized in situ as an intermediate to the desired ternary chalcopyrite material starting from the two reagents [Bu$^i_2$InSPr] and [Cu(S$_2$CNBu$_2$)$_2$] which must be combined in equimolar ratios. A number of analogous ternary CIS precursors were also synthesized by the reaction of alkyl indium thiolates with copper dithiocarbamates [Eq.3].

$$2RIn(SPr)_2 + 2Cu(S_2CNR'_2)_2 \rightarrow 2[RIn(SPr)_2Cu(S_2CNR'_2)] + (R'_2NCS_2)_2 \qquad [Eq.3]$$

However, only [Bu$_2$In(SPr$^i$)Cu(S$_2$CNPr$^i_2$)] was successfully implemented for depositing pure CuInS$_2$ by low pressure MOCVD. In the case of [BuIn(SPr$^i$)$_2$Cu(S$_2$CNR'$_2$)], tetragonal CuIn$_5$S$_8$ was deposited [Eq.4].

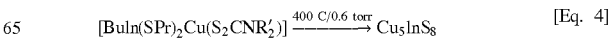

In continuing work, Buhro and Hepp were able to demonstrate that [{PPh$_3$}$_2$Cu(SEt)$_2$In(SEt)$_2$] could be utilized in a spray CVD process, for depositing thin-film CuInS$_2$ below 400° C. Hollingsworth, J. A., Hepp, A. F., Buhro, W. E., *Spray CVD of Copper Indium Disulfide Films: Control of Microstructure and crystallographic orientation*, Chem Vap. Deposition, 1999, 5, 105–108; Hollingsworth, J. A., Buhro, W. E., Hepp, A. F., Jenkins, P. P., Stan, M. A., *Spray chemical vapor deposition of CuInS2 thin films for application in solar cell devices*, Mat. Res. Soc. Symp. Proc., 1998, 495, 171–176; Harris, J. D., Hehemann, D. G., Cowen, J. E., Hepp, A. F., Raffaelle, R. P., Hollingsworth, J. A., *Using single source precursors and spray chemical vapor deposition to grow thin-film CuInS$_2$*, Proc. Of the 28th IEEE Photovoltaic Specialists Conference, Anchorage, Ak., 2000, 563–566. Thin films where deposited using a dual solvent system of toluene and dichloromethane, (CH$_2$Cl$_2$) as the carrier solvent. Single phase 112 orientated CuInS$_2$ thin films were deposited from [{PPh$_3$}$_2$Cu(SEt)$_2$In(SEt)$_2$] at a range of temperatures from 300 to 400° C., while at elevated temperatures (>500° C.), CuIn$_5$S$_8$ phase thin films were deposited. RBS EDS and XPS analysis showed that the films were free from any detectable impurities and highly crystalline, thus concluding the precursor decomposes cleanly. During the course of the study, the morphology of the deposited thin films where found to be temperature, and carrier solvent dependent. Films deposited at 300° C. and 350° C. yielded grain size of 400–800 nm, with smaller finer particles of 50–200 nm resident on top. At higher deposition temperature of 400° C., the films consisted of more angular and uniform grain size of approx 200 to 400 nm. Photoluminescence (PL) data and optical transmission measurements confirmed the deposited CuInS$_2$ thin films were direct band gap semiconductors.

SUMMARY OF THE INVENTION

A single source precursor for the deposition of ternary chalcopyrite materials is provided. The single source precursor has the empirical formula [{L}$_n$M'(ER)$_x$(X)$_y$(R)$_z$M"], wherein x is 1–4, x+y+z=4, L is a Lewis base that is coordinated to M' via a dative bond, n is greater than or equal to 1, M' is a Group I-B atom, M" is a Group III-A atom, E is a Group VI-A atom, X is a Group VII-A atom, and each R is individually selected from the group consisting of alkyl, aryl, vinyl, perfluoro alkyl, perfluoro aryl, silane, and carbamato groups. The single source precursor excludes the following
[{P(C$_6$H$_5$)$_3$}$_2$Cu(S—C$_2$H$_5$)$_2$In(S—C$_2$H$_5$)$_2$],
[{P(C$_6$H$_5$)$_3$}$_2$Cu(Se—C$_2$H$_5$)$_2$In(Se—C$_2$H$_5$)$_2$],
[{P(C$_6$H$_5$)$_3$}$_2$Cu(S(i-C$_4$H$_9$))$_2$In(S(i-C$_4$H$_9$))$_2$],
[{P(C$_6$H$_5$)$_3$}$_2$Cu(Se(i-C$_4$H$_9$))$_2$In(Se(i-C$_4$H$_9$))$_2$],
[{P(C$_6$H$_5$)$_3$}$_2$Ag(Cl)(SC{O}CH$_3$)In(SC{O}CH$_3$)$_2$],
[{P(C$_6$H$_5$)$_3$}$_2$Ag(Cl)(SC{O}C$_6$H$_5$)In(SC{O}C$_6$H$_5$)$_2$],
[{P(C$_6$H$_5$)$_3$}$_2$Ag(SC{O}CH$_3$)$_2$In(SC{O}CH$_3$)$_2$],
[{P(C$_6$H$_5$)$_3$}$_2$Ag(SC{O}C$_6$H$_5$)$_2$In(SC{O}C$_6$H$_5$)$_2$],
[{P(C$_6$H$_5$)$_3$}$_2$Cu(SC{O}C$_6$H$_5$)$_2$In(SC{O}C$_6$H$_5$)$_2$],
[{P(C$_6$H$_5$)$_3$}$_2$Cu(SC{O}C$_6$H$_5$)$_2$Ga(SC{O}C$_6$H$_5$)$_2$],
[{P(C$_6$H$_5$)$_3$}$_2$Ag(SC{O}C$_6$H$_5$)$_2$Ga(SC{O}C$_6$H$_5$)$_2$], and
[{P(C$_6$H$_5$)$_3$}$_2$Ag(SC{O}CH$_3$)$_2$Ga(SC{O}CH$_3$)$_2$].

A single source precursor for the deposition of ternary chalcopyrite materials is provided. The single source precursor is a liquid at room temperature and is effective to yield a ternary chalcopyrite material upon heating or pyrolysis of the single source precursor.

A method of depositing ternary chalcopyrite materials is also provided. The method includes the following steps:
a) providing a single source precursor for said ternary chalcopyrite having the empirical formula [{L}$_n$M'(ER)$_x$(X)$_y$(R)$_z$M"], wherein x is 1–4, x+y+z=4, L is a Lewis base that is coordinated to M' via a dative bond, n is greater than or equal to 1, M' is a Group I-B atom, M" is a Group III-A atom, E is a Group VI-A atom, X is a Group VII-A atom, and each R is individually selected from the group consisting of alkyl, aryl, vinyl, perfluoro alkyl, perfluoro aryl, silane, and carbamato groups, said single source precursor excluding
[{P(C$_6$H$_5$)$_3$}$_2$Cu(S—C$_2$H$_5$)$_2$In(S—C$_2$H$_5$)$_2$],
[{P(C$_6$H$_5$)$_3$}$_2$Cu(SC{O}C$_6$H$_5$)$_2$In(SC{O}C$_6$H$_5$)$_2$],
[{P(C$_6$H$_5$)$_3$}$_2$Cu(SC{O}C$_6$H$_5$)$_2$Ga(SC{O}C$_6$H$_5$)$_2$],
[{P(C$_6$H$_5$)$_3$}$_2$Ag(SC{O}C$_6$H$_5$)$_2$In(SC{O}C$_6$H$_5$)$_2$],
[{P(C$_6$H$_5$)$_3$}$_2$Ag(SC{O}C$_6$H$_5$)$_2$Ga(SC{O}C$_6$H$_5$)$_2$],
[{P(C$_6$H$_5$)$_3$}$_2$Ag(SC{O}CH$_3$)$_2$In(SC{O}CH$_3$)$_2$], and
[{P(C$_6$H$_5$)$_3$}$_2$Ag(SC{O}CH$_3$)$_2$Ga(SC{O}CH$_3$)$_2$];
and
b) depositing the single source precursor on a substrate using a spray CVD technique.

A method of making a single source precursor for the deposition of ternary chalcopyrite materials is also provided, the method including the step of carrying out the following reaction:

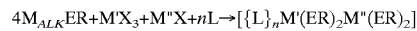

$$4M_{ALK}ER + M'X_3 + M"X + nL \rightarrow [\{L\}_n M'(ER)_2 M"(ER)_2]$$

wherein
$M_{ALK}$ is an alkali metal element,
E is a Group VI-A element,
R is selected from the group consisting of alkyl, aryl, vinyl, perfluoro alkyl, perfluoro aryl, silane and carbamato groups,
M' is a Group III-A element,
M" is a Group I-B element,
X is a Group VII-A element, and
n is greater than or equal to 1.

A method of making a quantum dot includes the steps of a) providing a single source precursor for a ternary chalcopyrite material; and b) pyrolyzing the single source precursor to yield a quantum dot made of ternary chalcopyrite material having dimensions less than 100 nanometers.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS OF THE INVENTION

Figure 1:
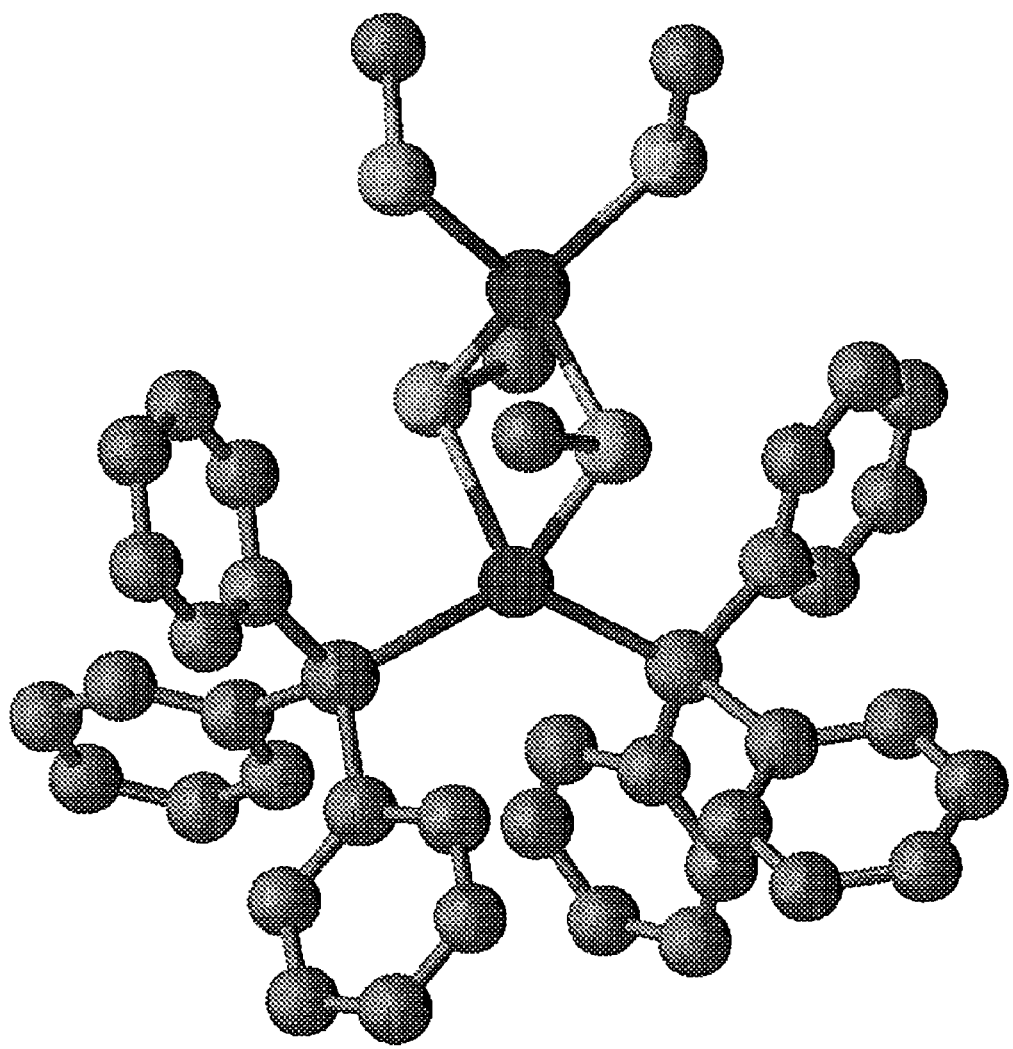
FIG. 1 is a single crystal X-ray resolved structure of a new SSP, [{PPh$_3$}$_2$Ag(SMe)$_2$In(SMe)$_2$], according to the invention which is useful to yield the semiconductors AgInS$_2$ and AgIn$_5$S$_8$ via pyrolysis.

As used herein, when a range such as 5–25 (or 5 to 25) is given, this means preferably at least 5 and, separately and independently, preferably not more than 25. Also as used herein, the following abbreviations used to refer to chemical structures/species have the following meanings: Ph=phenyl group; Et=ethyl group; Pr=propyl group; Bu=butyl group. Throughout the following description, and in the claims, the above abbreviations can be substituted for or with their empirical formula equivalents with no change in scope or meaning; i.e. Bu is the same as —C$_4$H$_9$, Ph is the same as —C$_6$H$_5$, etc.

The invention includes a single source precursor for ternary chalcopyrite materials useful as semiconductors, for example in solar collection cells. By "single source" it is meant that a precursor molecule according to the invention provides all of the necessary components (atomic species) in the appropriate stoichiometric ratios so that upon decomposition (e.g. by pyrolysis) of the precursor, a desired ternary chalcopyrite material is formed.

In a preferred embodiment, the single source precursors (SSP) of the present invention yield a ternary chalcopyrite material of the form I-III-VI$_2$, where roman numeral I refers to Group I-B from the periodic table, roman numeral III refers to Group III-A and roman numeral VI refers to Group VI-A. By ternary, it is meant that the chalcopyrite materials yielded or produced from the SSPs of the present invention contain atoms from three elemental Groups of the periodic table. For example, a ternary I-III-VI$_2$ chalcopyrite material has one atom from Group I-B, one atom from Group III-A and two atoms from Group VI-A, and therefore contains atoms from three Groups of the period table, satisfying the definition of a "ternary" chalcopyrite. CuInS$_2$ is an example of such a ternary chalcopyrite that can be produced from single source precursors according to the invention as will be further described.

It should be noted that ternary chalcopyrites include materials having multiple and/or different atoms from each of three Groups from the periodic table. For example, CuInSSe is a ternary chalcopyrite because it has Cu (Group I-B), In (Group III-A), and S and Se (both from Group VI-A). In addition, molecules of the form (Cu:Ag)(In:Ga)(S:Se), having various ratios of the respectively grouped atoms are all ternary chalcopyrites (Cu and Ag both are in Group I-B, In and Ga both are in Group III-A, S and Se both are in Group VI-A). In addition, these same ternary chalcopyrites can afford the following semiconductors of stoichiometry AgIn$_5$S$_8$ and CuIn$_5$S$_8$. In the case of the CuIn$_5$S$_8$ this is prepared when the SSPs are pyrolyzed at higher temperatures, e.g. greater than 600° C. In the case of AgIn$_5$S$_8$ its fabrication is dependent on the processing conditions, such as temperature, concentration, pressure etc.

Single source precursors according to the invention are in the form of one of the following structural formulas:

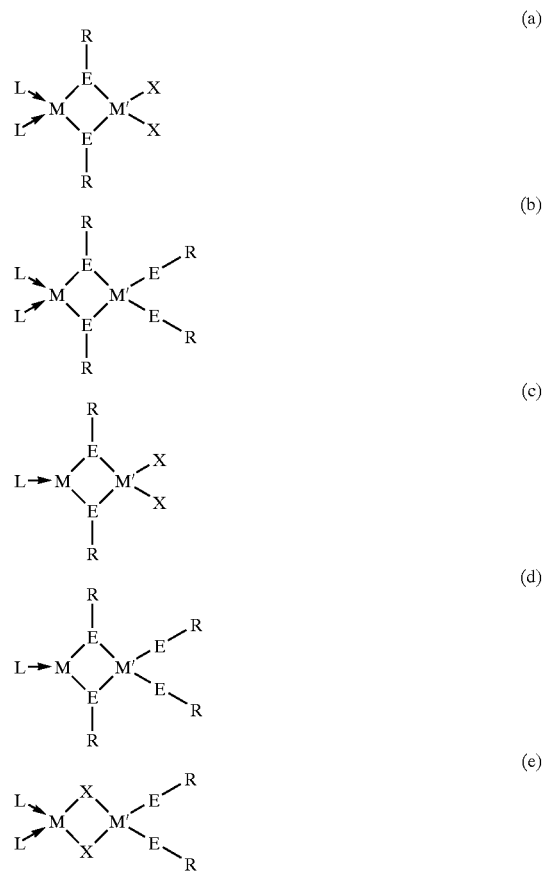

-continued

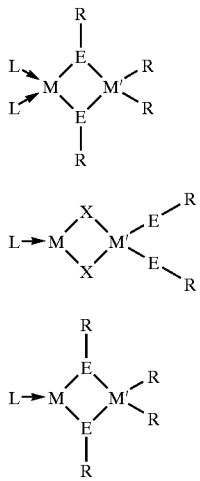

In the above structures (a)–(h),
L is a Lewis base that is coordinated to M' via a dative bond (indicated structurally by the arrows in each of the above-drawn structures),
M' is a Group I-B atom,
M" is a Group III-A atom,
E is a Group VI-A atom,
X is a Group VII-A atom, and
R is an alkyl, aryl, vinyl, perfluoro alkyl, perfluoro aryl, silane, or carbamato group.

Alternatively, a SSP according to the invention can have three E atoms (three ER groups) whereas structures (a)–(h) above have either 2 or 4 E atoms. To obtain a three-E atom structure, one can substitute any E-R group in either of structures (b) or (d) above with a halogen (x) atom.

All of the above structural formulas (a)–(h), including all three-E atom variants thereof described in the preceding paragraph, can be represented by the empirical formula $[\{L\}_n M'(ER)_x(X)_y(R)_z M"]$, wherein x is 1–4, x+y+z=4, n is greater than or equal to 1, preferably 1 or 2, and L, X, E, M' and M" are defined as above.

In the above SSP structures, it is not necessary that every R group is the same group (i.e. that they are all aryl or all alkyl, etc.). Different R groups can be individually selected and may be different from one another. This is important to note when using the empirical formula $[\{L\}_n M'(ER)_x(X)_y(R)_z M"]$ to represent the SSPs according to the invention because it must be understood that even though (ER) is grouped together as $(ER)_x$, each of the "x" Rs attached to an E atom is individually selected and can be different from all or several of the other R groups in the SSP molecule. Similarly, each of the "z" Rs is individually selected and can be different from all or several of the other R groups in the SSP molecule. For example, different R groups having different structure, MW, resonance characteristics, chirality, steric size, enzymatic, electronic, chemical and/or other properties can be selected for each R location in order to "tune" the SSP molecule as described in more detail below. Hence, it will be understood that as used herein, and in the claims, the empirical formula $[\{L\}_n M'(ER)_x(X)_y(R)_z M"]$ is not intended to require all R groups to be the same, and in fact each R group can be individually selected to be the same as or different from all or several of the other R groups. In a preferred embodiment, all R groups are selected to be the same group.

Each of the above SSPs is degradable (preferably via heating or pyrolysis as known in the art) to provide a ternary I-III-VI$_2$ chalcopyrite material of the form M'M"E$_2$. For example, in any of the above structures (a)–(h), when M' is selected to be copper (Cu), M" is selected to be indium (In) and E is selected to be sulfur (S), the resulting SSP will yield the ternary chalcopyrite CuInS$_2$ upon degradation of the SSP. In addition, structures (a) and (b) have been found to yield ternary I-III$_5$-VI$_8$ chalcopyrites of the form M'M"$_5$E$_8$.

It has been discovered by the inventors herein that, surprisingly and unexpectedly, suitable SSPs for ternary I-III-VI$_2$ chalcopyrite materials are not limited to those structures mentioned in the background section, but that suitable SSPs can be prepared according to any of above structural formulas (a)–(h).

The SSPs according to the invention are suitable for depositing thin film ternary I-III-VI$_2$ chalcopyrite layers via a spray CVD process. In particular, the number of "tunable" sites (particularly the R sites in the above structures) within the SSP provides a wide array of possible chemical and structural formulas for the SSPs according to the invention, which can be prepared or modified having varying compositions engineered to suit specific spray CVD processes. By selective manipulation of the steric and electronic properties of the functional groups, the SSP molecule essentially can be tuned to match the properties of a desired spray CVD process, including such thermal properties as decomposition temperatures and material phase.

In the SSP according to the invention, $[\{L\}_n M'(ER)_x(X)_y(R)_z M"]$ or specifically in any of the structures (a)–(h), the Lewis base(s), L, in each structure is/are selected to provide sufficient electron donation to stabilize the M' complex (which otherwise would be highly reactive and unstable) prior to solution pyrolysis of the SSP to yield the ternary chalcopyrite. The Lewis acid-base interaction is a valuable component to the overall stability of the SSP molecule, given that the ability of the Lewis base to dissociate from the cation at lower energies is pertinent to the degradation of the SSP at reduced temperatures. Hence, the Drago-Wayland approximation, can be used for ternary single source precursor design, to quantitatively estimate the strength of the Lewis acid-base interaction between the M' center and the neutral donor.

SSPs having Lewis bases of the form PPh$_3$ [P—(C$_6$H$_5$)$_3$] have been found to be readily synthesizable. When PPh$_3$ is used as the Lewis base, it is generally required that the SSP has two coordinating PPh$_3$ groups in order to provide sufficient basic power to stabilize the M' metallic center. SSPs having two coordinating Lewis base groups are shown in structures (a), (b), (e) and (f) above. Alternatively, if a stronger base is used, then only a single Lewis base group (a single 'L' group) may be used as shown in structures (c), (d), (g) and (h).

It will be understood that the above eight structural formulas for the invented SSPs can be divided into four groups of two structures each where the only difference between the two structures is the use of one versus two coordinating Lewis base groups. These groups are [(a) and (c)], [(b) and (d)], [(e) and (g)], and [(f) and (h)]. Thus the only difference between structure (a) and structure (c) is that structure (a) utilizes two Lewis base groups whereas structure (c) utilizes a single Lewis base group that is selected to have sufficient reducing power by itself to stabilize the M' Group I-B metallic center.

The above eight structural formulas for the invented SSPs can also be divided into a second set of four groups of two structures each as follows: [(a) and (b)], [(c) and (d)], [(e)

and (f)], and [(g) and (h)]. In this grouping, the difference between structures (a) and (b) is understood as follows. Structure (b) was the first generic structure of a SSP for a ternary I-III-VI$_2$ to be synthesized. When a SSP having structure (b) is pyrolyzed to yield M'M"E$_2$, all of the R groups are denatured or burned away leaving the two metallic centers M' and M", as well as two Group VI-A E atoms. During pyrolysis of the SSP, the bridging bonds, namely M'-E(R)-M" are cleaved more easily than those between terminal E atoms and M", (i.e. M"-E(R)). Once all the R groups and the bridging E atoms are removed, the Lewis base bound to the M' metallic center is dissociated, leaving behind M'. Thus via a redistribution mechanism M' is attracted and forms a bond to the M" metallic center having the two terminal E atoms already bonded thereto. This yields the ternary chalcopyrite, M'M"E$_2$. It has been discovered, surprisingly and unexpectedly, that an SSP can be prepared similarly to structure (b) except that the terminal E atoms are be replaced with Group VII-A (halogen) atoms, and that this terminal halogen-substituted structure can be pyrolyzed to yield the same M'M"E$_2$ ternary chalcopyrite as the SSP of structure (b). This terminal halogen-substituted structure is shown in structure (a).

Without wishing to be bound by a particular theory, it is believed that the formation of the ternary chalcopyrite M'M"E$_2$ is formed via a similar redistribution mechanism as described above when a SSP of structure (a) is pyrolyzed.

Due to the thermodynamically favorable formation of X$_2$, (which is evolved in the gaseous state) and the semiconductor M'M"E$_2$ through a redistribution mechanism, these are the prime products. When only one halogen X is present in the compositional formula for the SSP, then a redistribution mechanism is still believed to be prevalent but it now involves two molecules of the SSP, thereby obtain one halogen atom X from each of the two SSP molecules to thus afford X$_2$ in the gaseous state.

SSP structures (c) and (d) are structurally analogous respectively to (a) and (b), differing therefrom only based on whether one or two Lewis base groups are used to stabilize the M' center. Accordingly, structure (c) differs from structure (d) in that the terminal E atoms from structure (d) are substituted with X (halogen) atoms in structure (c).

SSP structures (e) and (f) are related in that only two Group VI-A "E" atoms are provided, but in structure (e) they are provided in the terminal position whereas in structure (f) they are provided in the bridging position. When the E atoms are provided in the terminal position (structure (e)), halogen atoms are provided in the bridging position to join the M' and M" metallic centers, through a delocalization of their charge as will be understood by a person of ordinary skill in the art. In effect, each bridging halogen X atom supplies half of its one electron density to each of the M' and M" atoms, leaving the overall charge on the halogen atom negative. When the E atoms are provided in the bridging position (structure (f)), no terminal halogen atoms need be provided. (If terminal halogens are provided, then the SSP would be of structure (a)).

SSP structures (g) and (h) are analogous respectively to structures (e) and (f) except that only one Lewis base group is provided to stabilize the M' center.

Most preferably, a SSP according to the invention has a structure of (a) or (b), less preferably of (c) or (d), less preferably (e) or (f), less preferably (g) or (h). This preferred structural hierarchy is due to experience with ease and readiness of preparation of the SSPs, and not to any perceived greater or lesser effectiveness of the SSP to yield the desired ternary I-III-VI$_2$ chalcopyrite material.

In a preferred embodiment, the SSPs according to the invention are prepared by the reaction of a stabilized Cu(I) cation, with an indium(III), or gallium(III) chalcogenide anion prepared in situ by reaction of the conjugate acid of the thiol, or selenol etc. with NaOEt in SCHEME 1:
Synthesis of ternary single source precursors

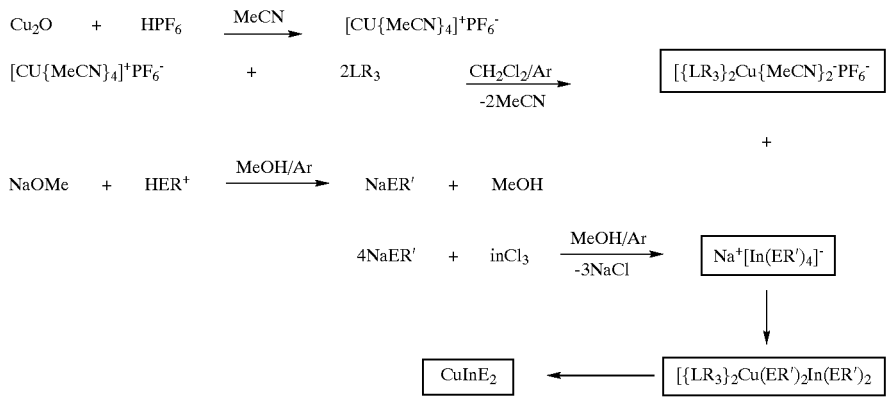

In Scheme 1 above, L, E, and R are defined the same as above, and R' can be defined similarly as R above.

In a further, more preferred embodiment, SSPs according to the invention are made via the novel reaction pathway illustrated below as Scheme 2.

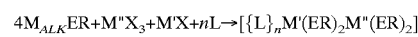

where:
M$_{ALK}$ is an alkali metal element,
E is a Group VI-A element,
R is selected from the group consisting of alkyl, aryl, vinyl, perfluoro alkyl, perfluoro aryl, silane and carbamato groups,
M' is a Group III-A element,
M" is a Group I-B element,
X is a Group VII-A element, and
n is greater than or equal to 1.

Scheme 2: Preferred Synthesis Reaction for Preparing Ternary I-III-VI$_2$ Chalcopyrite Materials In carrying out the above reaction (Scheme 2), the reactants are combined in the appropriate stoichiometric ratios under aerobic or anaerobic conditions. The reaction can be carried out in a batch or continuous process to yield the SSP according to the invention. Novel Scheme 2 eliminates the need to perform a cumbersome, and lengthy synthetic methodology and the need to employ expensive and/or non-commodity starting reagents. In addition, the new route has been shown to be mass scaleable which is important for commercial applications. These are novel and important features of the synthesis method of Scheme 2 above, compared to other methods of synthesizing SSPs.

Scheme 2 is a preferred method for preparing SSPs according to the invention because the reaction can be carried out using commercially available reagents under readily reproducible conditions as mentioned above. For example, reacting NaSCH$_3$ with InCl$_3$ and adding CuCl and 2PR$_3$, (all of which are commercially available or readily prepared, R=alkyl or aryl group) in a one-pot batch reaction vessel yields [{PR$_3$}$_2$Cu(SMe)$_2$In(SMe)$_2$] which is a SSP according to the invention of structural formula (b) above.

In a further example, the above Scheme 2 reaction pathway can be carried out to prepare the known ternary SSP [{P(C$_6$H$_5$)$_3$}$_2$Cu(SEt)In(SEt)$_2$] as follows. A 500 ml 3 neck flask is charged with NaOMe (0.5M, 346.19 mL, 173.095 mmol), and anhydrous methanol 200 mL. HSEt (10.76 g, 12.82 mL, 173.095 mmol), is added to the reaction flask via syringe and left for 5 minutes. InCl$_3$ (9.34 g, 42.218 mmol) is rapidly added, resulting in a clear solution (on some occasions small white flocculent ppt is also observed). The mixture is stirred and allowed react for 15–30 minutes. A solution, or suspension of anhydrous CuCl (4.60 g, 46.440 mmol), and PPh$_3$ (24.36 g, 92.880 mmol), in a mixture of anhydrous CH$_3$CN/CH$_2$Cl$_2$ (3:1 volume ratio), is rapidly added to Na$^+$[In(SEt)$_4$]$^-$ formed in situ. An important feature of this Scheme 2 is the in situ formation of the ionic complex [L$_{(n)}$M"(CH$_3$CN)$_{(4-n)}$]$^+$ as an intermediate to the final ternary chalcopyrite product. After 24 hours the reaction is concentrated, the product extracted with CH$_2$Cl$_2$ (200 mL) and filtered through Celite. Evaporation of the filtrate affords the SSP precursor. A similar preparative route is used for the preparation of the Ag analogues, but in the absence of light. In the case of liquid SSPs, they can be extracted using pentane.

The versatility of this synthetic pathway is illustrated by the ability to modulate the physical properties of the SSP and composition at any of the intermediate synthetic steps by adjusting the Lewis acid-base interaction (L→Cu), and/or adjusting the accessibility of the lone pair of electrons on the neutral donor ligand by variation of R, adjusting the bond strength between the chalcogenide with either In/Ga and Cu metal centers. The preferred pathway of Scheme 2 is further characterized by the ability to prepare SSPs containing analogues of group VI-A elements, (S, Se, Te), and the ability to prepare SSPs using either indium or gallium as the Group III-A element.

SSPs of the type [{L}$_2$M'(ER)$_2$M"(ER)$_2$] (structure (b) above) have been shown to be excellent candidates for depositing ternary I-III-VI$_2$ semiconductors, which has been established as a key component for the fabrication of the next generation of photovoltaic (PV) devices. For example current solar cells based on CuInS$_2$ and CuInSe$_2$ have shown efficiencies that are comparable to single crystal PV devices. The versatility of the [{L}$_2$M'(ER)$_2$M"(ER)$_2$] architecture is demonstrated by the ability to manipulate its composition, thermal and solid state properties for depositing wide band gap semiconducting materials.

One of the important parameters in developing the above Scheme 2 pathway was to maintain the flexibility of synthesis to permit tailoring of the SSP as described above. Using the Scheme 2 pathway the ternary SSP [{PPh$_3$}$_2$Cu($\mu$SePh)$_2$In($\mu$SePhMe)$_2$] and a new SSP [{PPh$_3$}$_2$Cu($\mu$SMe)$_2$] were prepared in good yields with the exception that NaSePh and NaSMe were used. Further versatility of the pathway was examined for the preparation of the analogous Ag SSP to [{PPh$_3$}$_2$Ag($\mu$SMe)$_2$In($\mu$SMe)$_2$].

Under the absence of light the Lewis based stabilized Ag(I) metal center was prepared in situ by the reaction of AgNO$_3$ with 2 equivalents of PPh$_3$ in CH$_3$CN/CH$_2$Cl$_2$ and added directly to the indium thiolate prepared in situ. After 24 hours the product was worked up as a white crystalline material. NMR and elemental analysis confirmed the product to be [{PPh$_3$}$_2$Ag($\mu$SMe)$_2$In($\mu$SMe)$_2$].

Crystals of the [{PPh$_3$}$_2$Ag($\mu$SMe)$_2$In($\mu$SMe)$_2$] SSP suitable for single-crystal X-ray diffraction studies, obtained by controlled growth from a biphasic solvent system of CH$_2$Cl$_2$/hexane at room temperature overnight, led to the determination of the structure as shown in FIG. 1.

Figure 2:
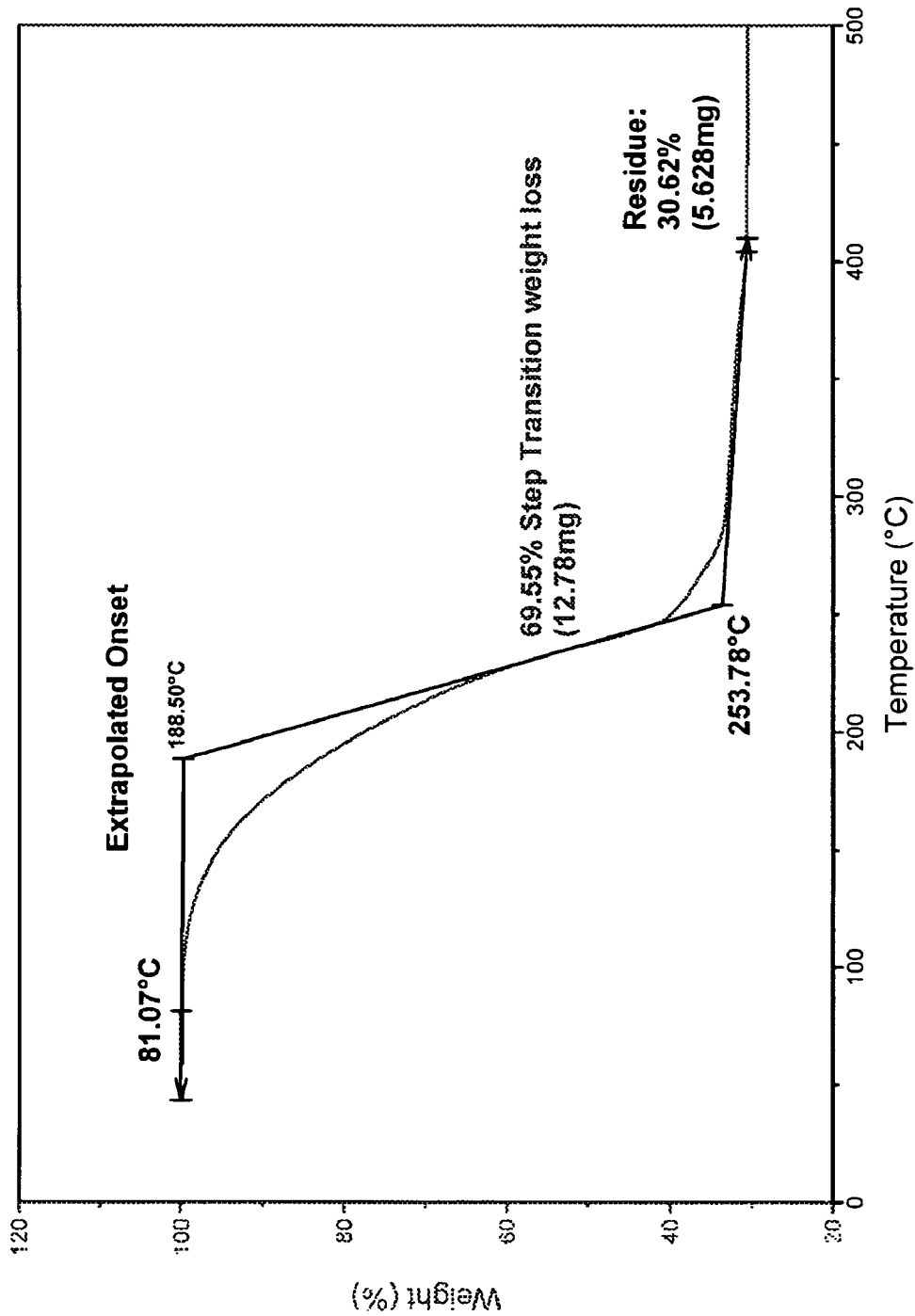
FIG. 2 shows TGA profiles for [{P(n-Bu)$_3$}$_2$Cu(SEt)$_2$In(SEt)$_2$], SSP 7 from Table 1 herein.

Multinuclear NMR data have demonstrated that SSPs made according to the above reaction pathway (Scheme 2) were free from any starting reagents. Thermogravimetric analyses (TGA) were performed at ambient pressure in platinum pans on samples of the synthesized SSPs, heated at a rate of 10° C./min under a dinitrogen atmosphere. Weight loss was associated with decomposition of the complexes. Calculation of the derivative maximum rate of weight loss (%/° C.), listed as MRW in Table 1, shows a range from a low of 225° C. for sample 8 to a high of 325° C. for sample 5. Calculation of the precursor efficiency to afford CIS/Se as the final product, based on the residual material from the TGA experiments found the samples to be within 5% (FIG. 2).

TABLE 1

Thermal data for ternary single source precursors prepared by reaction pathway of Scheme 2.

| Single Source Precursors [{L}$_2$Cu(ER)$_2$M(ER)$_2$] | TGA | | | DSC | |
| --- | --- | --- | --- | --- | --- |
| | Onset ° C. | MRW** ° C. | Residue % | M.P. ° C. | Dec. ° C. |
| 1 [{PPh$_3$}$_2$Cu(SEt)$_2$In(SEt)$_2$] | 236 | 269 | 25 | 122 | 266 |
| 2 [{AsPh$_3$}$_2$Cu(SEt)$_2$In(SEt)$_2$] | 205 | 233 | 18 | 47 | 276 |
| 3 [{SbPh$_3$}$_2$Cu(SEt)$_2$In(SEt)$_2$] | 212 | 239 | 26 | 45 | 271 |
| 4 [{PPh$_3$}$_2$Cu(SPr$^i$)$_2$In(SPr$^i$)$_2$] | 215 | 254 | 29 | 163 | 260 |

TABLE 1-continued

Thermal data for ternary single source precursors prepared by reaction pathway of Scheme 2.

| Single Source Precursors [{L}$_2$Cu(ER)$_2$M(ER)$_2$] | TGA | | | DSC | |
|---|---|---|---|---|---|
| | Onset °C. | MRW** °C. | Residue % | M.P. °C. | Dec. °C. |
| 5 [{PPh$_3$}$_2$Cu(SPh)$_2$In(SPh$_2$] | 261 | 325 | 22 | 117 | 280 |
| 6 [{PPh$_3$}$_2$Cu(SePh)$_2$In(SePh)$_2$] | 233 | 253 | 22 | 53 | 219 |
| 7 [{P(Bu$^n$)$_3$}$_2$Cu(SEt)$_2$In(SEt)$_2$] | 189 | 238 | 27 | — | 264 |
| 8 [{P(Bu$^n$)$_3$}$_2$Cu(S(Pr$^n$))$_2$In(SPr$^n$)$_2$] | 171 | 225 | 22 | — | 239 |
| 9 [{PBu$_3$}$_2$Cu(SePh)$_2$In(SePh)$_2$] | 229 | 255 | 25 | * | * |
| 10 [{PPh$_3$}$_2$Cu(SMe)$_2$In(SMe)$_2$] | 221 | 254 | 27 | 164 | 242 |
| 11 [{PPh$_3$}$_2$Ag(SMe)$_2$In(SMe)$_2$] | 229 | 272 | 29 | 141 | 238 |
| 12 [{PBu$_3$}$_2$Ag(SEt)$_2$In(SEt)$_2$] | 187 | 239 | 30 | — | 285 |

*not recorded;
**Max value listed

Figure 3:
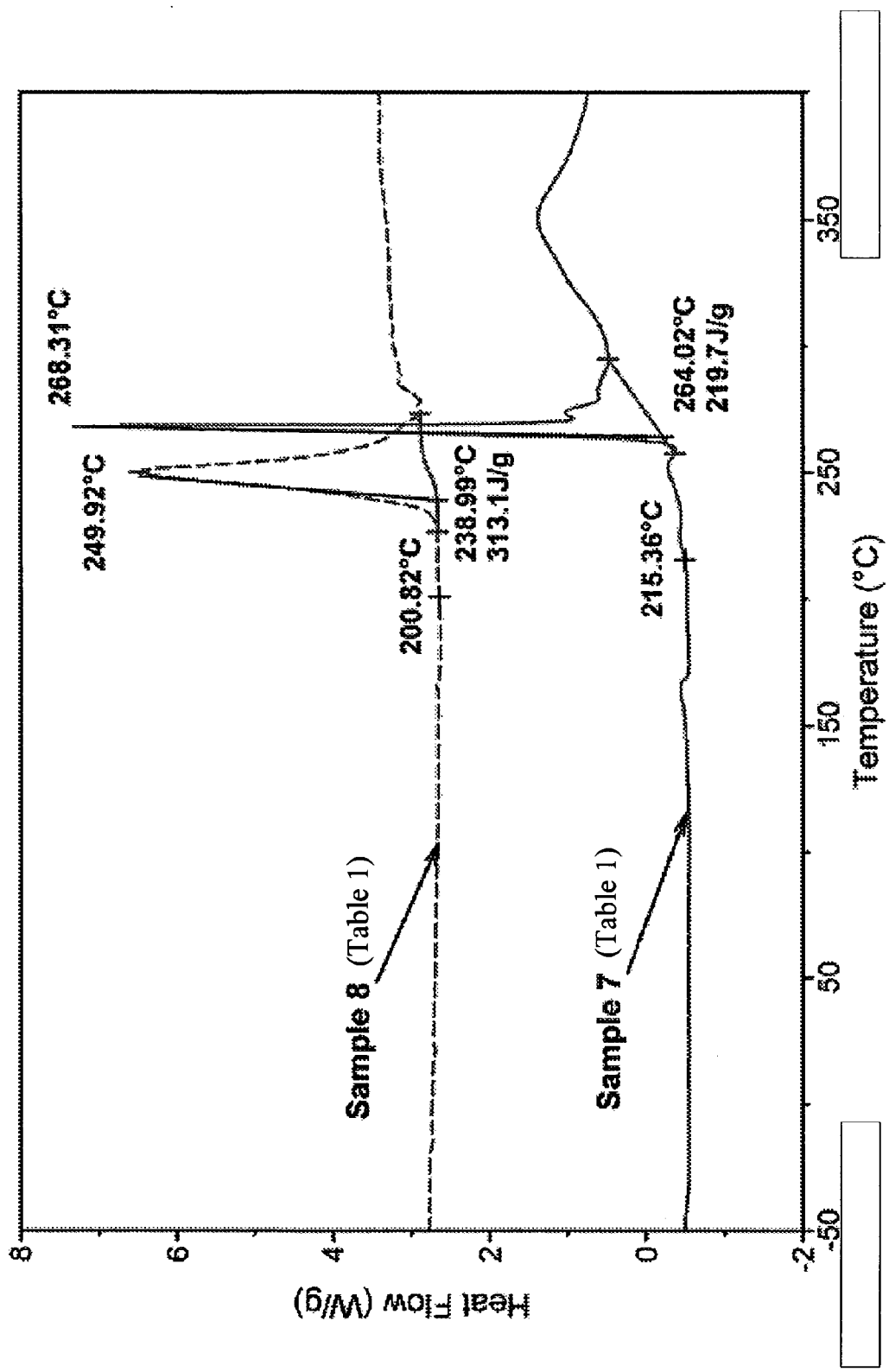
FIG. 3 shows the results of low temperature DSC for [{P(Bu$^n$)$_3$}$_2$Cu(SEt)$_2$In(SEt)$_2$] and [{P(Bu$^n$)$_3$}$_2$Cu(S(Pr$^n$))$_2$In(SPr$^n$)$_2$] SSPs according to the invention (SSPs 7 and 8 from Table 1 herein), which are liquid at room temperature.

A further example of the flexibility of the [{L}$_2$M'(ER)$_2$M"(ER)$_2$] architecture to direct adjustment of these precursors are SSPs 7 and 8 from Table 1, which are the first ternary single source precursors for the deposition of CuInS$_2$ which are in the liquid state at room temperature (T=25° C.). Preferably, SSPs that are liquid phase at room temperature according to the invention have Lewis base (L) group(s) with a large or bulky steric structure, such as strait chain alkyl groups having at least three C atoms. It is believed the steric hindrance contributed by such Lewis base groups (e.g. the butyl groups in SSPs 7 and 8 above) cause or result in the molecule being in the liquid phase at room temperature. Low temperature DSC was used to investigate the liquid phase for SSPs 7 and 8. In separate studies, SSPs 7 and 8 were subjected to both quench cooling and slow controlled cooling before being heated at 10 and 5° C./min. In low temperature DSC experiments using controlled and quench cooling, both samples 7 and 8 were found not to show an endotherm assignable to a melting phase transition thus confirming their liquid phase at ambient temperatures (FIG. 3).

Examination of the other phase transitions reveal the main exothermic events for SSPs 7 and 8 begin with extrapolated onset temperatures of 264° C. and 239° C. (from DSC experiments), which represent the decomposition of the samples. TGA profiles for [{P(Bu)$_3$}$_2$Cu(SEt)$_2$In(SEt)$_2$], SSP 7 from Table 1 above, are shown in FIG. 2.

Figure 11:
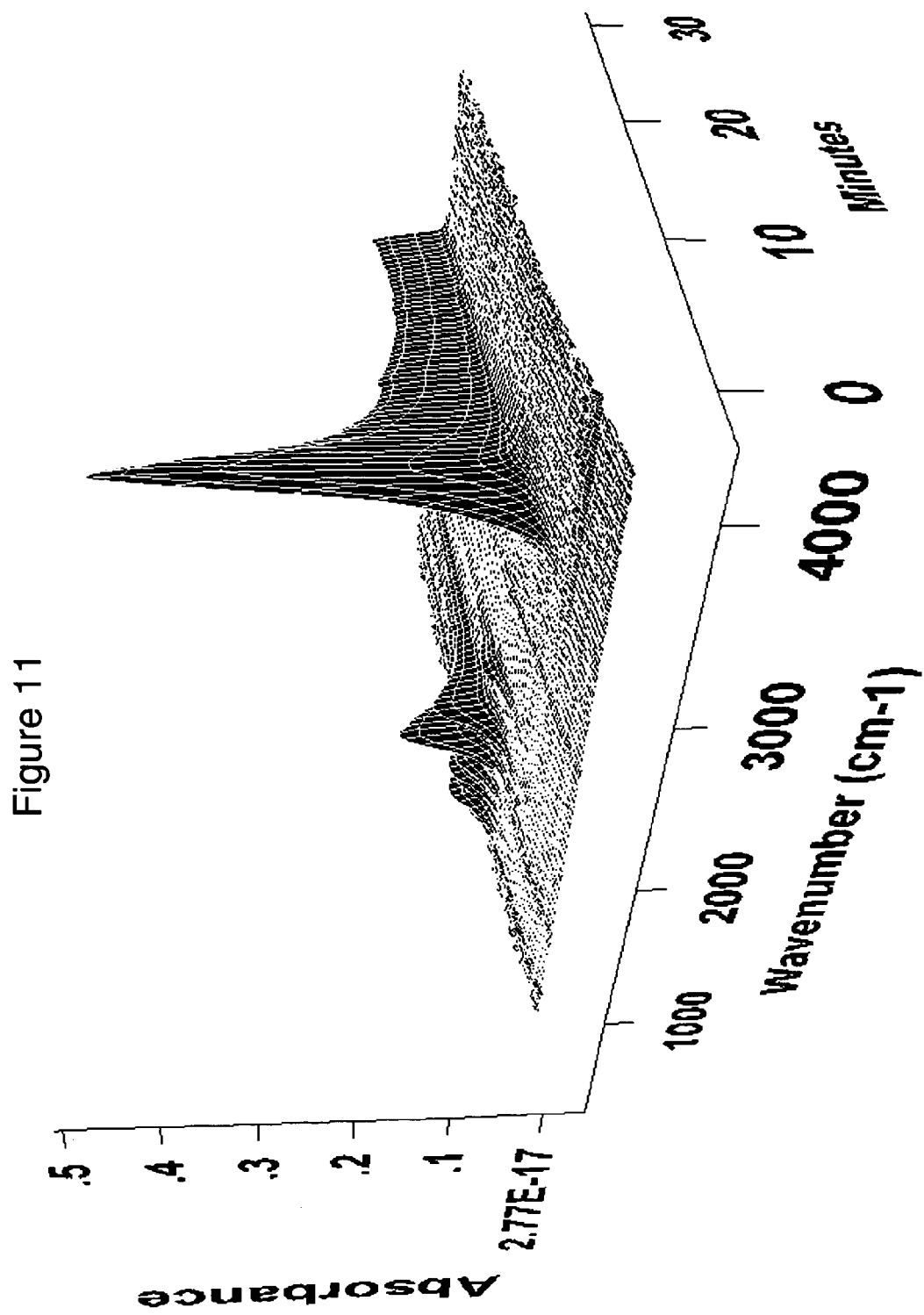
FIG. 11 shows the EGA-FTIR spectrum for [{P(n-Bu)$_3$}$_2$Cu(SEt)$_2$In(SEt)$_2$], SSP 7 from Table 1 herein.
Figure 12:
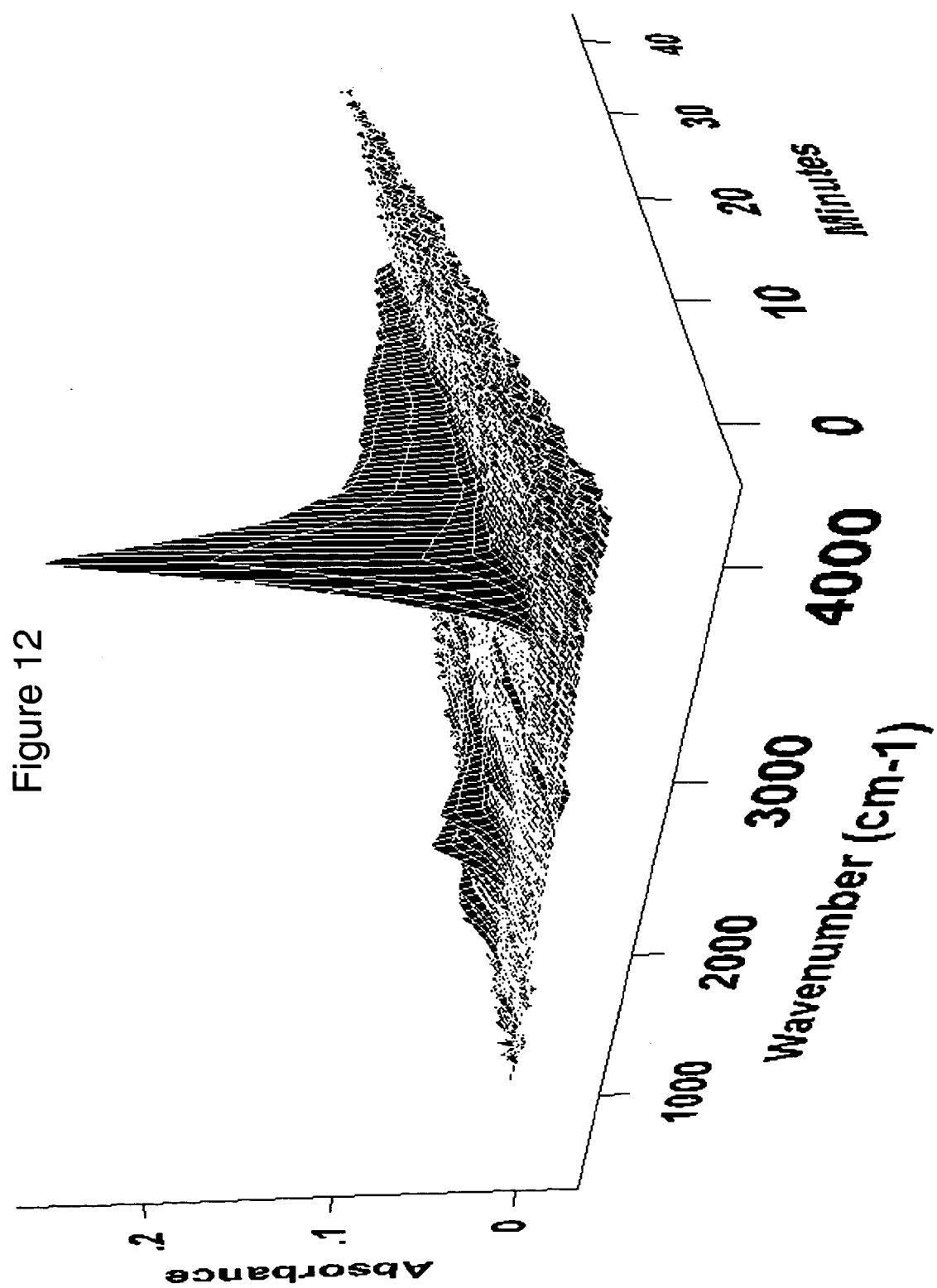
FIG. 12 shows the EGA-FTIR spectrum for [{P(n-Bu)$_3$}$_2$Cu(SPr$^n$)$_2$In(SPr$^n$)$_2$], SSP 8 from Table 1 herein.

The ability of the new precursors to thermally decompose to yield single-phase CIS (CuInS$_2$) was investigated by powder X-ray diffraction (XRD) analysis and Energy Dispersive Spectroscopy (EDS), on the non-volatile solids from the TGA experiments of selective compounds. Furthermore, using TGA-Evolved Gas Analysis, the volatile components from the degradation of the SSPs could be analyzed via real-time FTIR and mass spectroscopy, thus providing information for the decomposition mechanism. The examination of the real time FTIR and Mass spectra confirm that the SSP decompose by cleavage of the weaker bridging bonds and the extrusion of R$_2$S, followed by the loss of the Lewis base. (see FIGS. 11 and 12 for SSPs 7 and 8 respectively).

Figure 13:
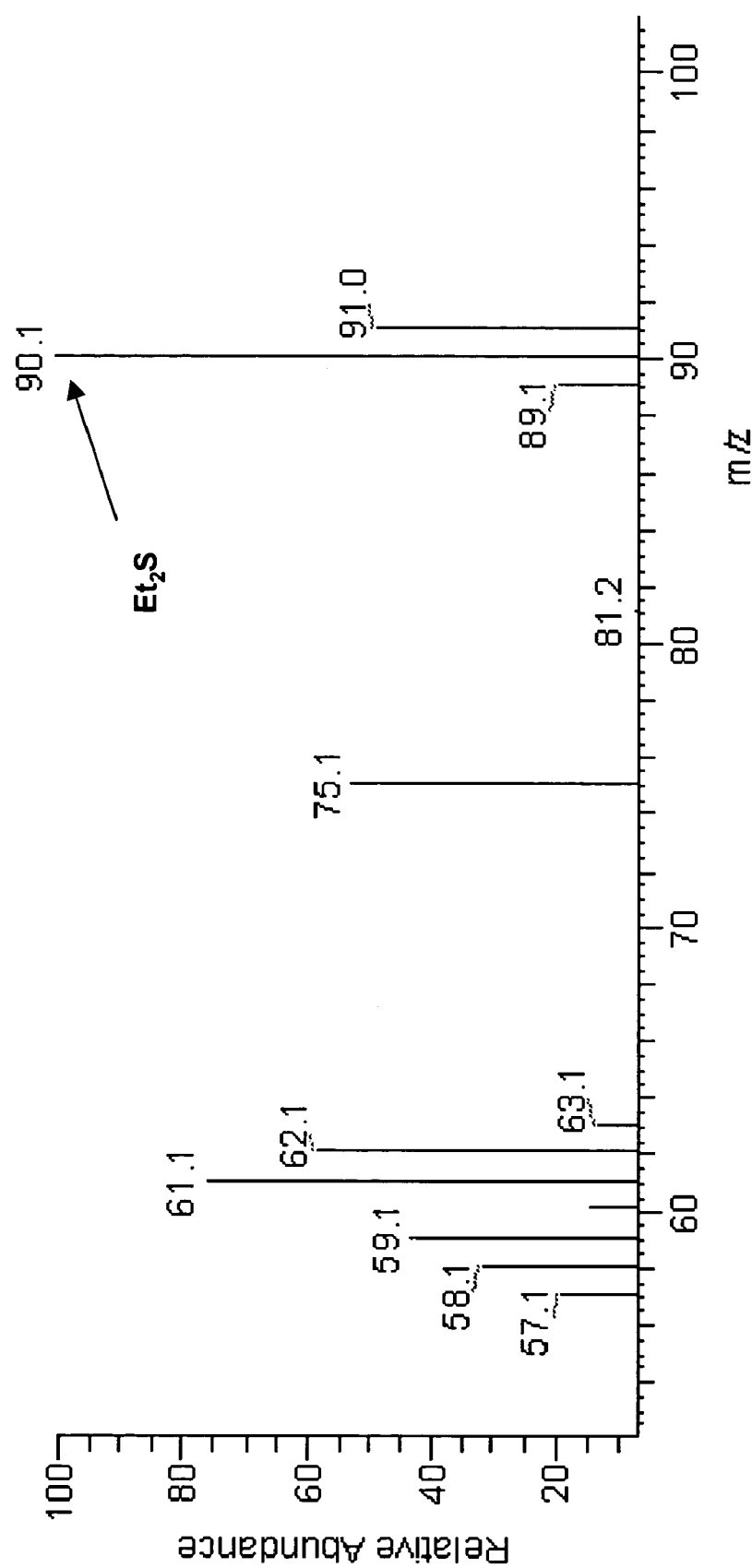
FIGS. 13 and 14 show EGA-MS (EI) data for [{P(n-Bu)$_3$}$_2$Cu(SEt)$_2$In(SEt)$_2$], SSP 7 from Table 1 herein.
Figure 14:
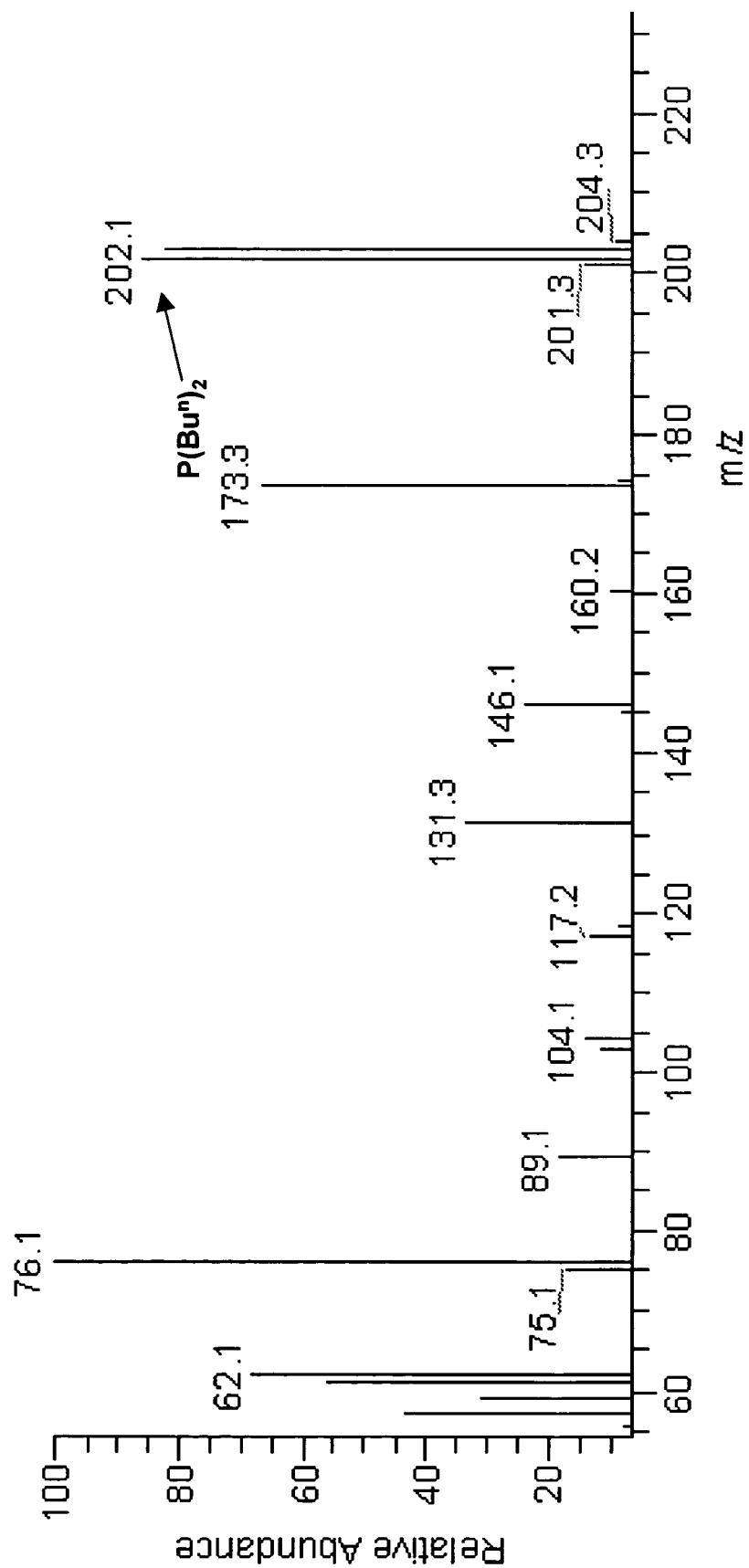
Figure 15:
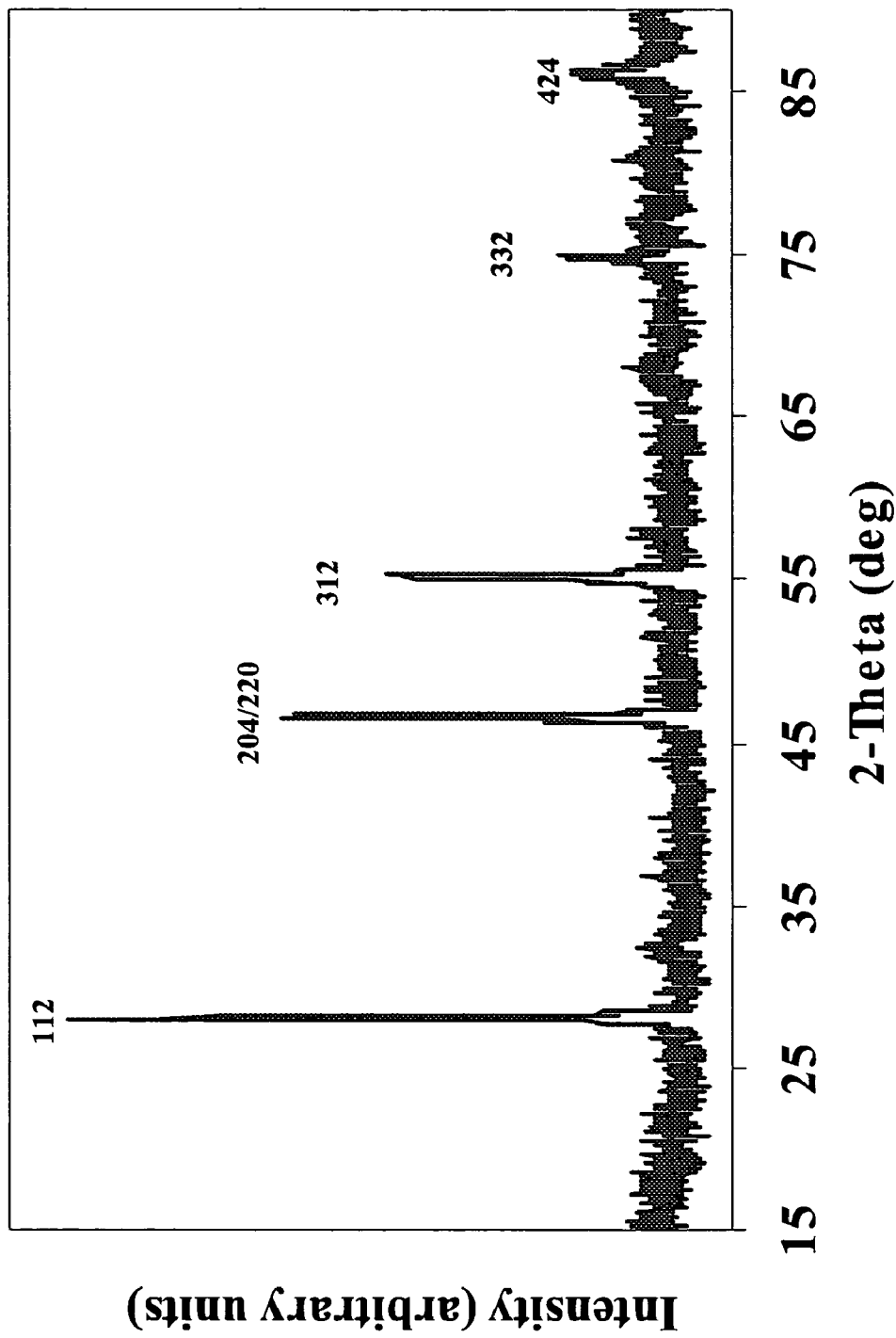
FIG. 15 is an XRD powder diffraction spectrum for non-volatile residue from pyrolysis of [{P(n-Bu)$_3$}$_2$Cu(SEt)$_2$In(SEt)$_2$], SSP 7 from Table 1 herein (Cu K$\alpha$, 1.541 Å).

For example, for SSP 7 namely [{P(Bu)$_3$}$_2$Cu(SEt)$_2$In(SEt)$_2$], Correlation with the EGA-mass spectra allowed for the assignment to the initial loss of diethyl sulfide, as supported by the library fit and from the assignment of the fragment and parent ions (m/z=90) (FIG. 13). After approximately 15 minutes mass-spec EGA shows the absence of peaks assignable to Et$_2$S and the occurrence of fragment ions with a mass to charge ratio (m/z) greater then 90 with an intense peak at m/z=202. These can be assigned to the successive loss of PBu$_3$ on the basis of its library fit of 92% and assignment of the fragment ions (FIG. 14). XRD spectra for the non-volatile material produced from the pyrolysis of SSP 7 with the JCPDS reference patterns for CuInS$_2$ (27-0159), confirmed it to be single-phase CuInS$_2$ (see FIG. 15). Examination of the EDS spectra for the same samples shows predominant emissions due to Cu, In, and S edges, with the approximate percentage atomic composition of 27, 23 and 50 for 7 and 28, 23 and 49 for 8 respectively, thus supporting the formation of CuInS$_2$.

In addition to SSPs 7 and 8 from Table 1, two additional SSPs for ternary chalcopyrite materials have been isolated which are in the liquid state at room temperature: {P(Bu)$_3$}$_2$Cu(SePh)$_2$In(SePh)$_2$] and [{P(Bu)$_3$}$_2$Ag(SEt)$_2$In(SEt)$_2$].

Figure 4B:
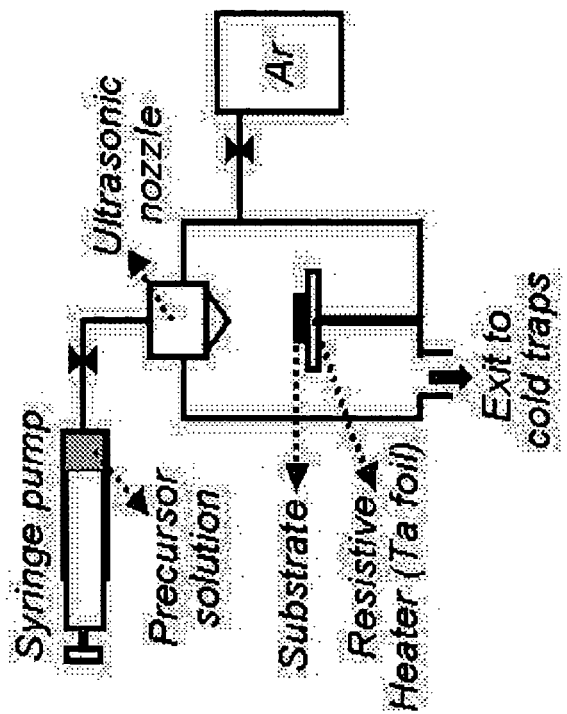
FIG. 4b is a schematic diagram of a vertical cold wall spray CVD reactor for the deposition of ternary SSPs according to the invention.
Figure 4A:
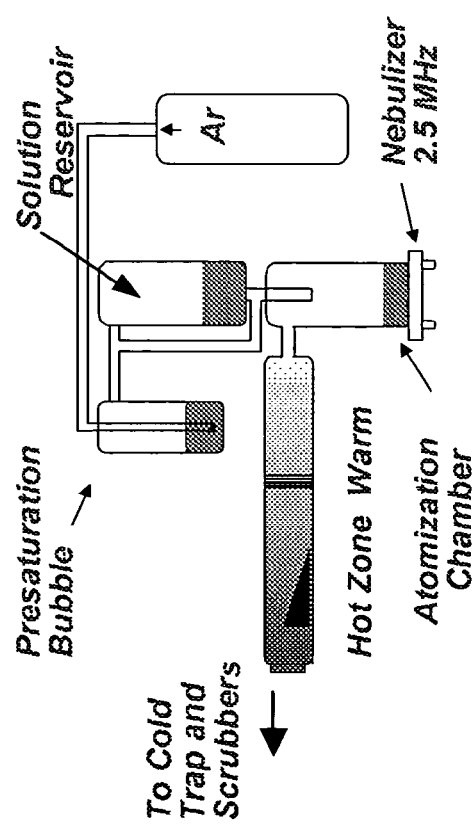
FIG. 4a is a schematic diagram of a horizontal hot wall spray CVD reactor for the deposition of ternary SSPs according to the invention.

Preferably, the SSPs according to the invention degrade to yield the desired I-III-VI$_2$ ternary chalcopyrite at a temperature less than about 500, preferably less than 480, preferably less than 460, preferably less than 440, preferably less than 420, preferably less than 400, preferably less than 380, preferably less than 360, degrees Celsius. The low degradation temperatures of the SSPs (compared to ~800° C. or greater for conventional, multi-source precursors where two or three precursors must be combined in appropriate stoichiometric ratios) make the SSPs disclosed herein well suited for spray CVD application techniques to deposit ternary chalcopyrites as mentioned above. Spray CVD has become an advancing technique where a room temperature precursor solution is ultrasonically nebulized or atomized, and is swept into hot wall reactor, (in this case a two zone hot wall reactor, the first is a "warm zone" to drive of the solvent and the second is the "hot zone" for film deposition) (FIG. 4a). The carrier-solvent (if present) is evaporated in the warm zone, and the atomized SSP is decomposed in the hot zone, where film growth occurs as in conventional CVD. As explained in the next paragraph, spray CVD techniques minimize the need for high volatility and temperature requirements for the SSP, which are essential in metal-organic chemical vapor deposition processes (MOCVD), by delivering the precursor to the furnace as an aerosol propelled by a fast-flowing carrier gas at low temperature. The latter feature of low temperature is an important benefit since volatizing the SSP is the conventional mode of introducing the SSP into the vapor phase. However, for thermally unstable, or SSP with no, or very little vapor pressure (as in this case), the high temperatures necessary to volatilize the SSP would prematurely decompose the SSP. Therefore spray CVD is the most suitable mode of CVD processes for fabricating thin films from these SSPs, however thin films can be fabricated from the SSPs according to the invention via other, less preferred CVD techniques as well.

In a spray CVD technique, the SSP (whether liquid at $T_{amb}$ or a solid or liquid dissolved in a suitable solvent) is atomized into tiny droplets forming a vapor mist which is deposited in the gas phase onto the substrate to be coated with the ternary chalcopyrite on degradation of the SSP. Thus, the need for the precursor(s) and associated solvent(s) to be highly volatile, and the need to deposit the precursor(s) at high temperature in order to vaporize the precursor(s) (both required for MOCVD), are eliminated. The result is that lower temperature decomposing precursors, such as the SSPs according to the invention, can be efficiently and effectively utilized to apply a uniform ternary chalcopyrite coating on a substrate surface via a low temperature spray CVD technique.

It has been found that ternary $I-III-VI_2$ chalcopyrite films applied via spray CVD using a ternary SSP according to the invention exhibit a highly oriented (112) phase. The phase of the deposited layer can be modified from (112) oriented to (204) oriented by tuning various spray CVD parameters such as vacuum, film thickness, SSP concentration, carrier gas flow rate, etc., and selecting appropriate spray CVD parameters to achieve a crystallite having the desired phase orientation is within the skill level of a person having ordinary skill in the art.

A thin film study was performed using two spray CVD techniques to apply ternary chalcopyrites from a SSP according to the invention. In the first study, the SSP was atomized and aerosolized with a suitable carrier gas using a horizontal hot wall reactor (FIG. 4a) and in the second study a vertical cold wall reactor (FIG. 4b) was used. In the hot wall reactor, the aerosol was generated by a 2.5 MHz plate nebulizer, and in the cold wall reactor a 120 kHz atomizing nozzle (Sono-Tek) was used. The aerosol was delivered into each of the reactors by argon carrier gas with a typical flow rate of 4 L/min. The hot wall reactor had two heating zones, the evaporation zone 130° C. and the deposition zone 400° C.

An automated syringe pump was used to deliver the precursor solution to the vertical cold-wall reactor at a flow rate of 1.5 mL/min, and the substrate temperature was held at about 400° C. The substrate was typically either conventionally soda-lime glass, or Corning 7059, or commercial molybdenum foil, but suitable substrates are not limited to these materials.

Films of $CuInS_2$ were deposited on polished fused silica, Kapton™, stainless steel, molybdenum, nickel, titanium, and polybenzobisoxazole (PBO) substrates using each spray CVD reactor. For a typical deposition in the hot wall reactor, 1.5 grams of the ternary single source precursor was dissolved in 150 ml of toluene. The solution was atomized by a 2.5 MHz nebulizer and swept into a two-zone hot-wall reactor by a carrier gas (argon) that was presaturated with the solvent. The substrate (10×76 mm), was mounted on an inclined silicon carbide coated graphite holder, which was centered in the hot-zone. The temperature of the first, warm zone (evaporation zone) was 128±1° C. and the temperature of the second, hot zone (deposition zone) was 390±1° C., with an argon carrier gas flow rate of 4 L/min. After deposition, the films were annealed at 600±1° C. for 10 minutes, unless otherwise noted. Films were then characterized by thin film spectroscopic techniques, which are within the skill level of a person having ordinary skill in the art.

Figure 5:
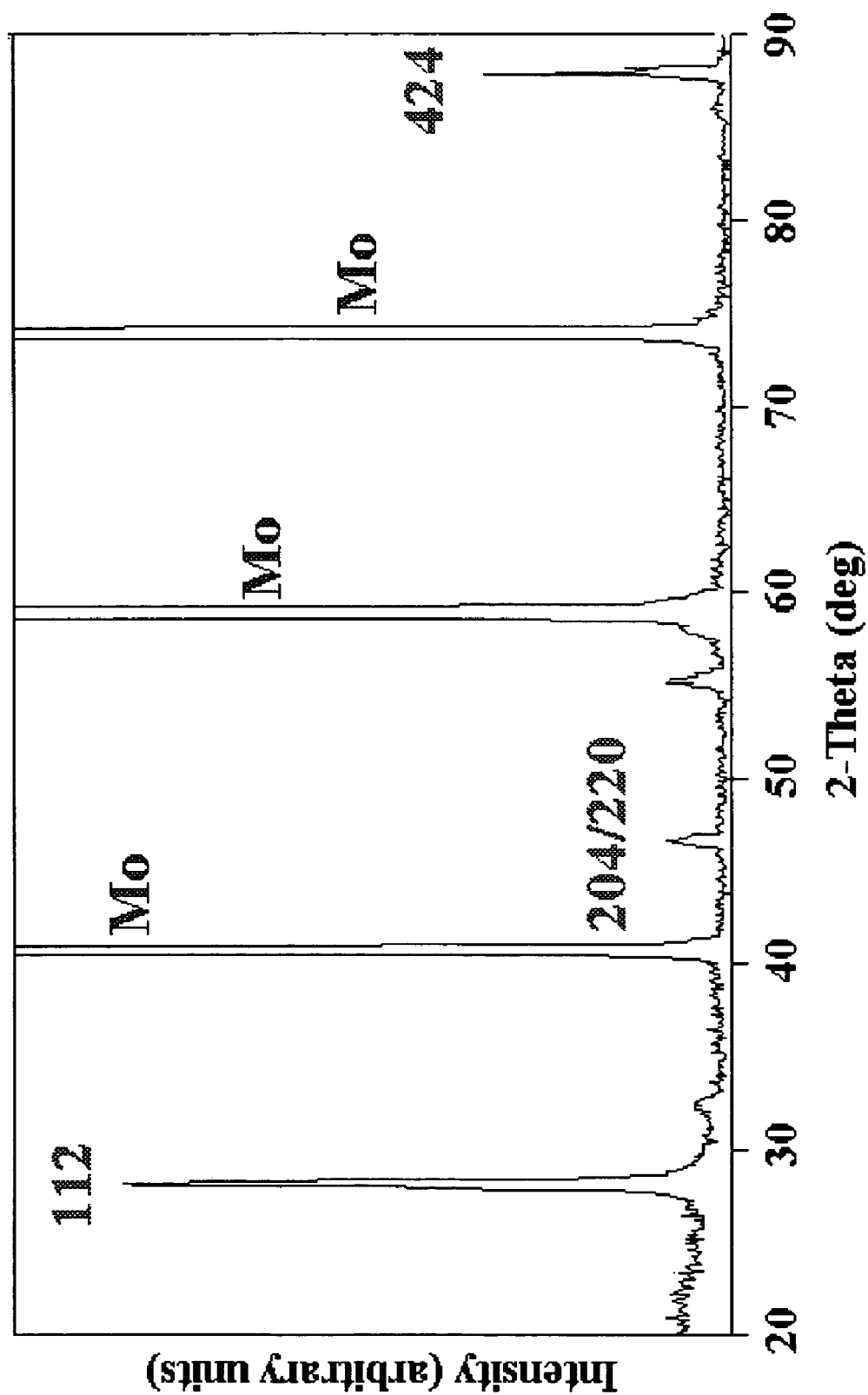
FIG. 5 is an X-ray powder diffraction spectrum of a CuInS$_2$ thin film deposited on molybdenum foil using the liquid SSP [{PBu$_3$}$_2$Cu(SEt)$_2$In(SEt)$_2$] according to the invention.

Well adhering films of $CuInS_2$ were deposited on a molybdenum substrate by spray CVD at 390° C. using $[\{PBu_3\}_2Cu(SEt)_2In(SEt)_2]$ (a liquid at room temperature), which were dark blue/black, due to variation in film thickness. As deposited, the $CuInS_2$ film was highly (112) oriented (FIG. 5).

Measurements of the atomic composition of the film using Energy Disperive Spectroscopy (EDS) were limited to Cu and In edges since the EDS emissions for sulfinur and Molybdenum overlapped. SEM-EDS data on a number of regions on the thin film gave atomic percents representative of $CuInS_2$ (see Table 2 below), and no evidence of phosphorous or carbon contamination could be detected, verifying the precursor decomposed cleanly. In Table 2, Front 1 and Front 2 refer to two points on the leading edge of the film to gas flow for the deposited semiconductor, and Back refers to the trailing edge of the deposited film with respect to gas flow.

TABLE 2

Atomic composition of $CuInS_2$ (CIS) thin-film deposited using $[\{PBu_3\}_2Cu(SEt)_2In(SEt)_2]$.

| | Atomic %, (±3%) | | |
|---|---|---|---|
| | Front 1 | Front 2 | Back |
| Cu | 50 | 51 | 50 |
| In | 50 | 49 | 50 |

Figure 6:
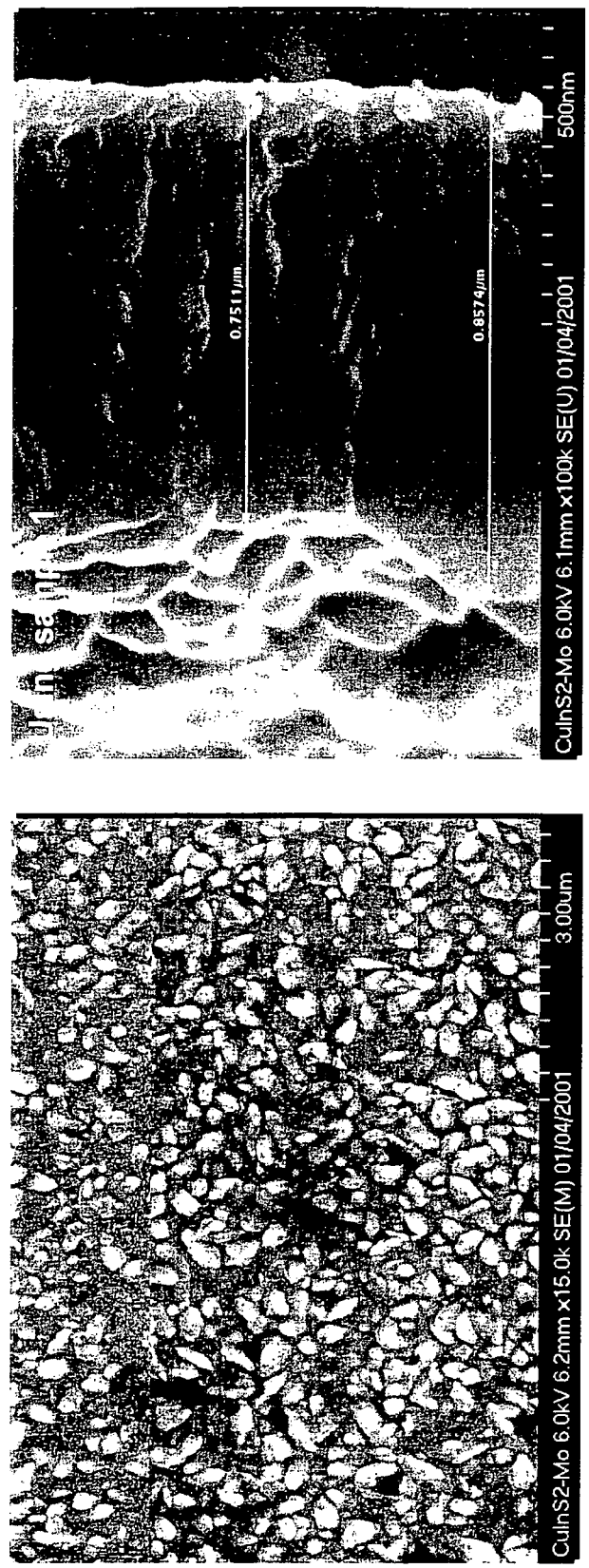
FIG. 6 shows SEM micrographs of a deposited CuInS$_2$ thin film using the SSP [{P(PPh)$_3$}$_2$Cu(SEt)$_2$In(SEt)$_2$] (SSP 1 from Table 1 herein).

SEM micrographs of the deposited $CuInS_2$ layer are provided in FIG. 6.

The electrical properties of the deposited films using $[\{PPh_3\}_2Cu(SEt)_2In(SEt)_2]$ were evaluated by current verses voltage (IV) measurements recorded for the thin films using thermally evaporated aluminum contacts (10 mm²), to make Schottky barrier diodes. The electrical properties of deposited films using SSP 1 from Table 1 $[\{PPh_3\}_2Cu(SEt)_2In(SEt)_2]$ showed SSP 1 to make excellent Schottky barriers. Following deposition of the films, the substrate-film was annealed at 600° C. The results are provided in FIG. 7.

Figure 7:
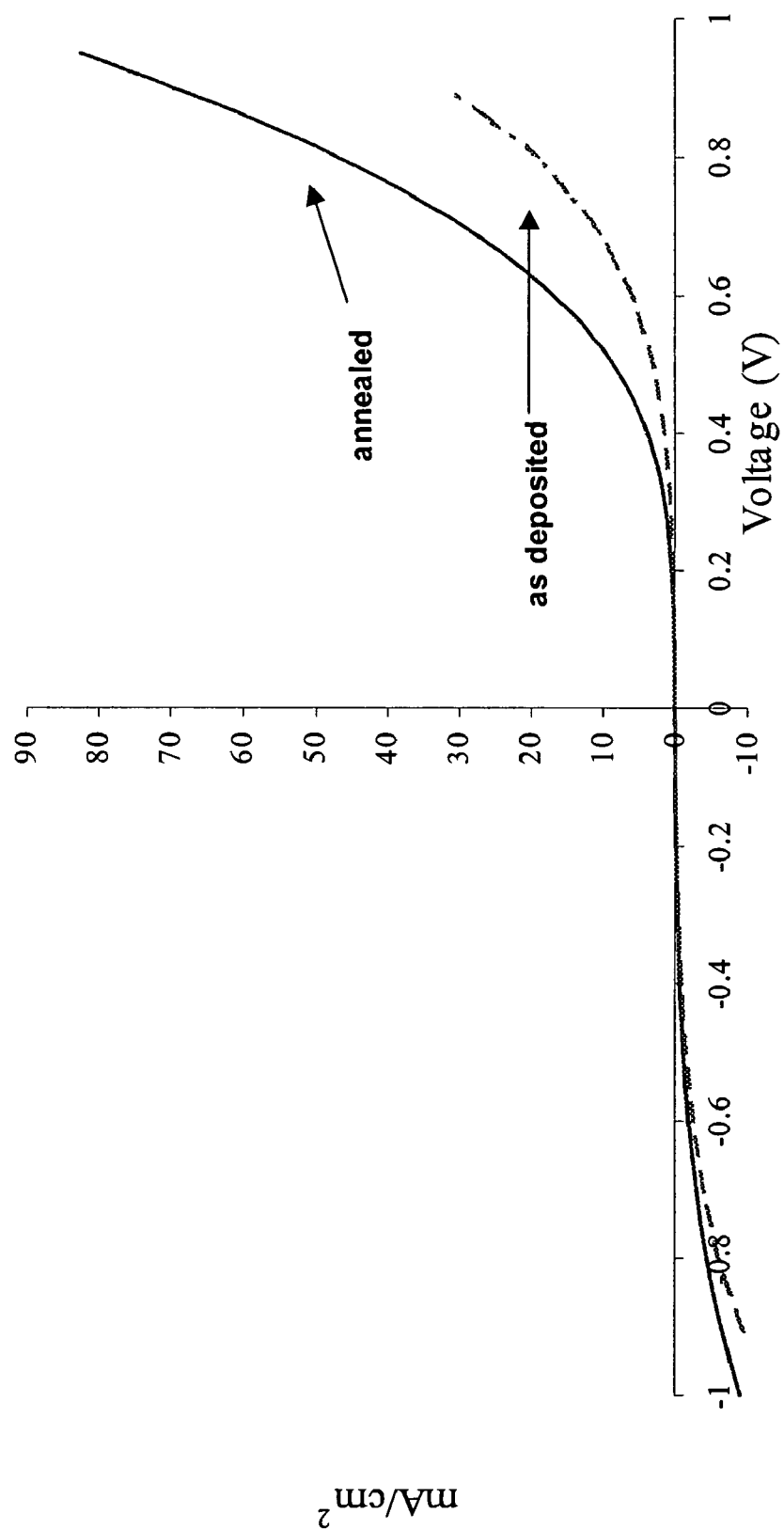
FIG. 7 shows a current density vs. voltage plot of a Schottky barrier made from evaporated Al on CuInS$_2$ on Mo foil using the SSP [{P(PPh)$_3$}$_2$Cu(SEt)$_2$In(SEt)$_2$] (SSP 1 from Table 1 herein).

As seen in FIG. 7, the Schottky barriers were excellent diodes on films annealed at 600° C., with "turn on" voltages of 0.6–0.8 V, with minimal reverse bias leakage. However, many of the contacts on the as-deposited films gave large reverse bias currents and nearly ohmic responses. This behavior was indicative of degeneracy of the semiconductor due to a high carrier density resulting from native defects. The improvement in the diode behavior of the annealed films is attributed to enhanced crystallinity and reduction of defects.

Figure 8:
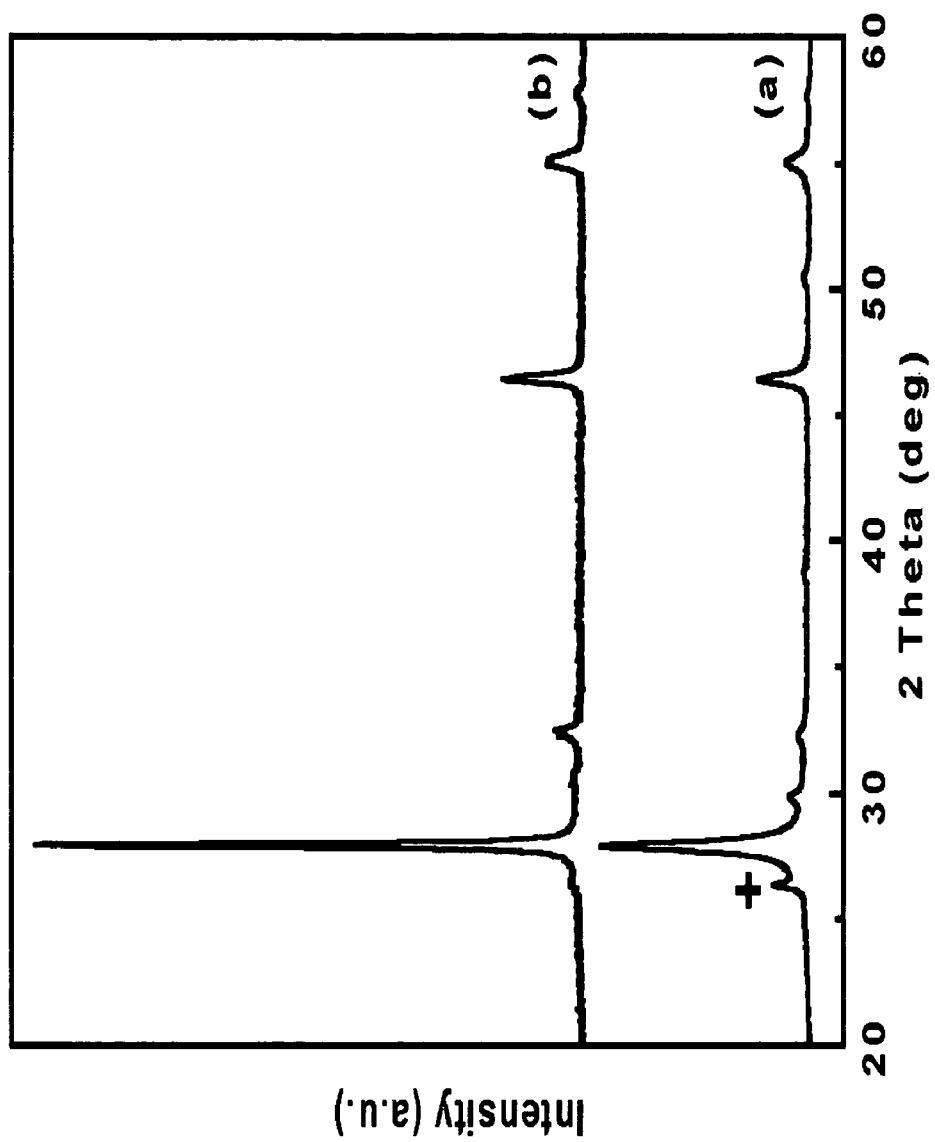
FIG. 8 shows the XRD pattern of a CuInS$_2$ film grown in a cold-wall reactor at 400° C. using [{PBu$_3$}$_2$Cu(SEt)$_2$In(SEt)$_2$]; graph (a): as-grown and graph (b): after annealing at 600° C. for 10 minutes under N$_2$ flow.

The flexibility of the SSPs according to the invention in spray CVD techniques has been further demonstrated by their use in a cold wall vertical Spray CVD reactor as described above. The XRD data obtained from the film grown using $[\{PBu_3\}_2Cu(SEt)_2In(SEt)_2]$ in the cold-wall reactor revealed the typical tetragonal chalcopyrite $CuInS_2$ phase with a 112 preferred orientation. The XRD pattern for the film grown in the cold-wall reactor from $[\{PBu_3\}_2Cu(SEt)_2In(SEt)_2]$ is shown in FIG. 8(a), and revealed the typical tetragonal chalcopyrite $CuInS_2$ phase with a weak (112) preferred crystal phase orientation including minor non detrimental phase(s) with the highest intensity at $2\theta=26.3°$(marked by '+'). Post-annealing at 600° C. for 10 minutes under $N_2$ flow was very effective to remove the secondary phase while also improving the crystalline quality of the $CuInS_2$ phase as shown in FIG. 8(b).

Figure 9:
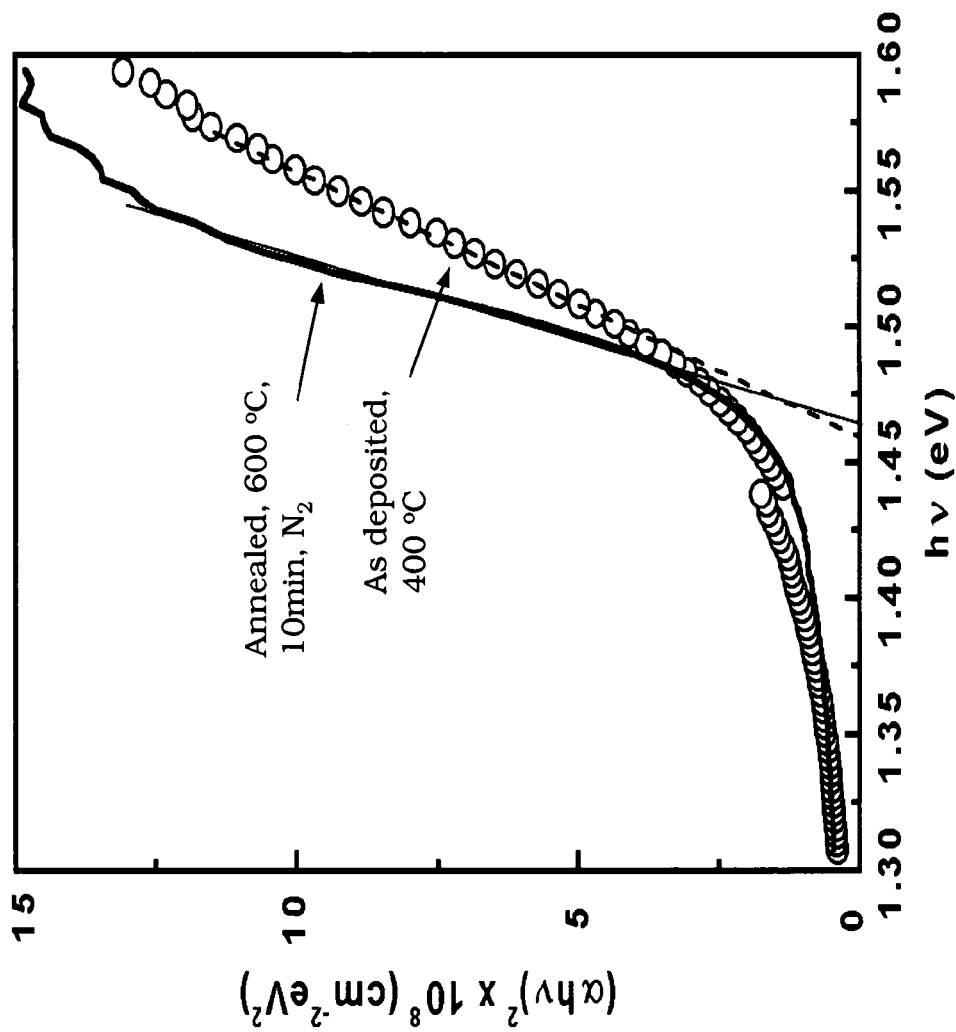
FIG. 9 shows a plot of $(\alpha E)^2$ vs. E for a CuInS$_2$ film grown from [{PBu$_3$}$_2$Cu(SEt)$_2$In(SEt)$_2$] in a cold-wall reactor, ($\alpha$ is an absorption coefficient estimated from the optical transmittance data and E is a photon energy).
Figure 10:
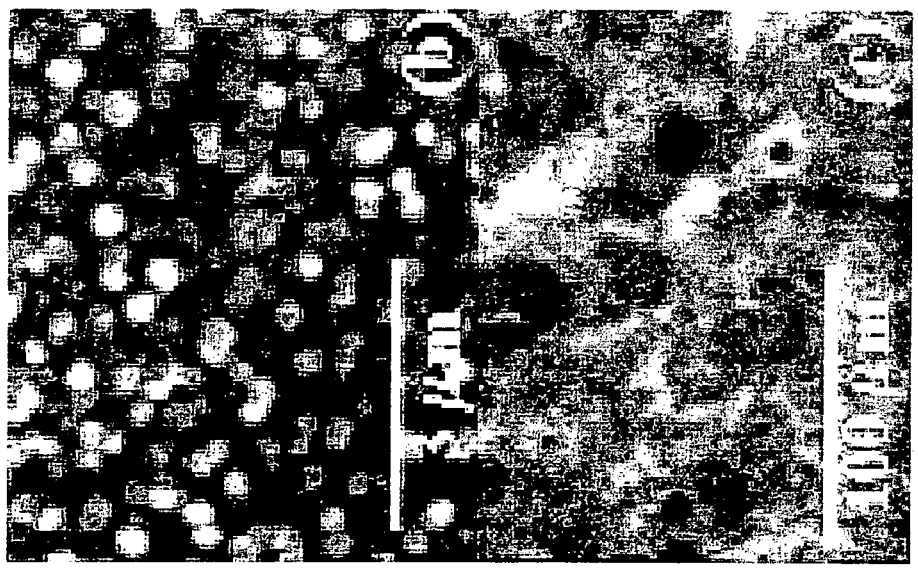
FIG. 10 shows an SEM micrograph of the CuInS$_2$ thin film of FIG. 9; (b) shows an SEM plane-view image of the film grown in the cold-wall reactor, and (c) shows an optical microscopic image of (b) with a low magnification.

The band gap for the film grown from the liquid precursor $[\{PBu_3\}_2Cu(SEt)_2In(SEt)_2]$, derived from a plot of $(\alpha E)^2$ vs. E (FIG. 9), was found to be ~1.46 eV. Although annealing the film showed a shift to a higher gradient band edge (current densities), it was found to have minimal effect on the observed band gap. SEM-EDS analysis showed the $CuInS_2$ thin-film to be near stoichiometric with atomic percents for Cu, In, and S as 26, 24, and 50 (±3%), respectively {FIG. 10}.

A substantial advantage to the liquid phase SSPs (e.g. SSPs 7 and 8 from Table 1 above) is that they have been found to be highly soluble in a wide range of organic solvents, including both polar and non-polar organic solvents. Such a wide range of solubility greatly enhances and simplifies the selection of appropriate solvents (when used) to suit a particular application or substrate. It is believed the observed solubility of the liquid phase SSPs according to the invention in both polar and non-polar organic solvents may be attributed to their ionic character and to the long non-polar alkyl chains.

By utilizing SSPs according to the invention, ternary I-III-VI$_2$ chalcopyrites can be provided by a lower temperature, less costly, non-toxic and comparatively simple procedure compared to conventional multi-source techniques. The ternary I-III-VI$_2$ that can be produced via pyrolysis of one of the invented SSPs, or of a mixture of at least two of the invented SSPs e.g., to yield a semiconductor of the form (Cu:Ag:Au)(Al:In:Ga)(S:Se:Te)$_2$. In such an SSP, it will be understood by persons of ordinary skill in the art that the ratios of Al:In:Ga and S:Se:Te can each be independently varied such that the overall stoichiometric composition of the semiconductor remains 1:1:2, (or some desirable SSPs, 1:5:8) to produce ternary chalcopyrite semiconducting materials having tunable band gaps between the conduction and valence bands. For example, the ratios could be designed to yield a ternary chalcopyrite material having a band gap of about 1.5 eV ($CuInS_2$), or about 2–2.4 eV ($CuGaS_2$)(but not limited to such). In another embodiment, ternary semiconductors of the form (Cu:Ag:Au)$_1$(Al:In:Ga)$_1$(S:Se:Te)$_2$ can be prepared from SSPs according to the invention where the ratios of Cu:Ag:Au, Al:In:Ga and S:Se:Te all can be varied or tuned to provide a semiconductor having a tunable band gap, e.g. in the range of from approx 0.5–3.5 eV.

Figure 16:
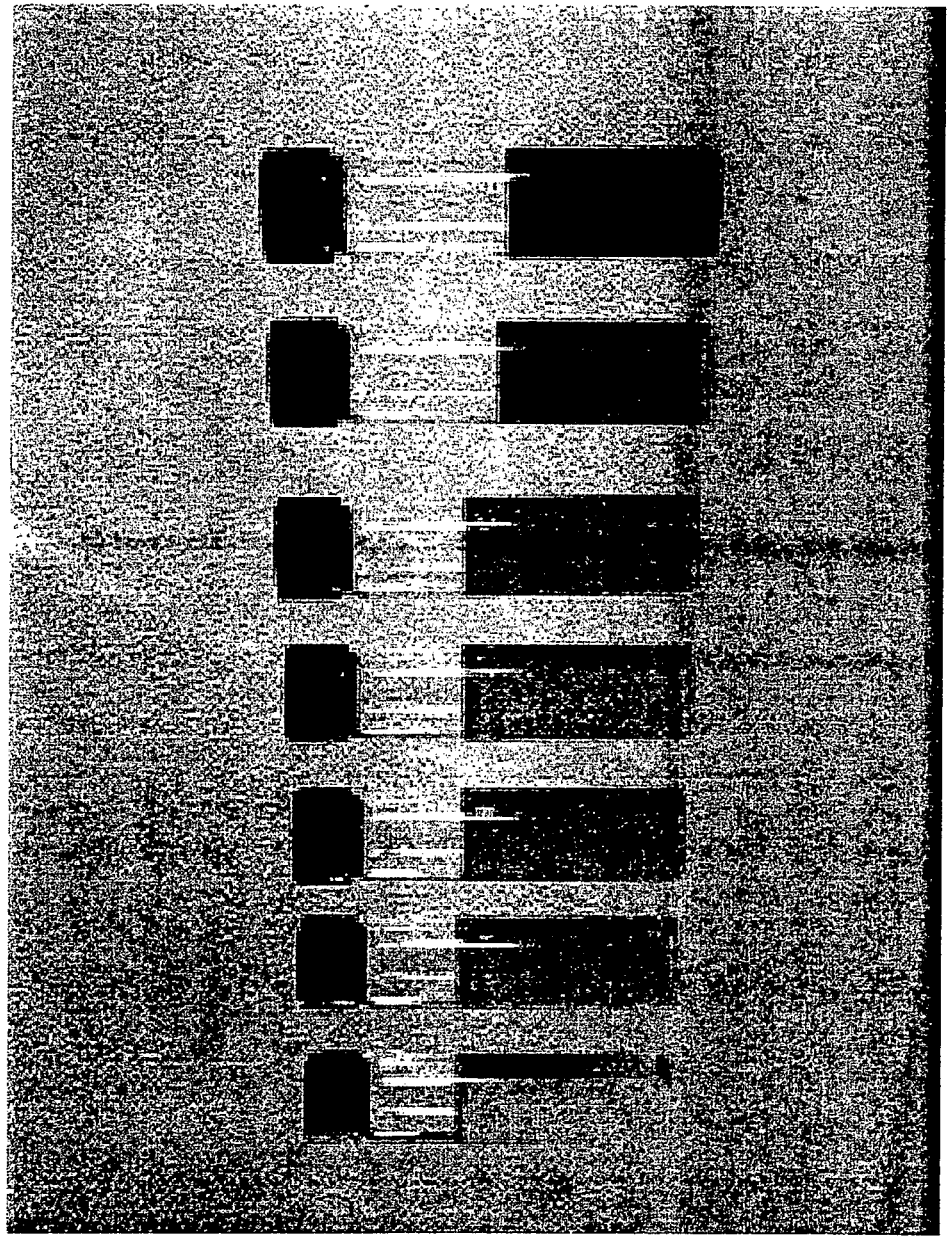
FIG. 16 shows seven vials of quantum dots of the same compound in solution, each vial containing quantum dots of different size.

In a preferred application, the SSPs according to the invention can be used to prepare nanocrystallites of ternary I-III-VI$_2$ chalcopyrite materials by first forming nanometric particulates or droplets of the SSPs and then pyrolyzing these droplets to yield the ternary chalcopyrite. Nanocrystallites, commonly referred to as quantum dots (QDs), are materials on the order of $10^{-9}$ m (1 nanometer) magnitude that posses properties unlike those of their analogous bulk solids. Quantum dots exhibit extraordinary optical properties that can be readily customized by changing the size and/or composition of the quantum dots. For example, by simply adjusting the size of the quantum dots, their absorption and emission spectra can be tuned to particular applications. This property of quantum dots is very unique in that a change in particle size, and not composition, effects a substantial, tangible and quantifiable change in their optical absorption and emission properties. An example of this property of quantum dots is provided in FIG. 16, where vials of quantum dots of the same material but having various sizes in suspension are shown. The size-dependence of the emittance color of the respective quantum dot suspensions can be clearly seen from FIG. 16. These unique properties have seen a rapid incorporation for their use in certain areas such as photovoltaics, biosensors, labeling type devices etc.

Conventional preparation of quantum dots is based on in situ pyrolysis of molecular reagents, which contain the desired elemental components, be it one molecule containing all the atoms for the semiconducting quantum dot, or multiple reagents containing at least one of the atoms, e.g.

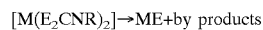

[M(E$_2$CNR)$_2$]→ME+by products

MCl+EPR$_3$→ME+by products

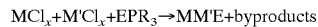

MCl$_x$+M'Cl$_x$+EPR$_3$→MM'E+byproducts

[M(E$_2$CNR)$_2$]+[M'(E$_2$CNR)$_2$]→MM'E+by products where

M, M'=metal & M≠M' (e.g. Cd, Zn, Cu, In, Ga etc.),

E=main group atom (e.g. P, As, S, Se, Te etc.),

ME, MM'E=semiconducting quantum dots.

In order to control the size of the quantum dots, i.e. obtain monodispersed quantum dots, the surface of the quantum dots needs to be passivated soon after preparation in order to prevent further nucleation with neighboring quantum dots. This is conventionally achieved by preparing the quantum dots in the presence of a passivating coordinating solvent/ligand. The hot solvent/ligand not only serves as a medium for the formation of the quantum dots via pyrolysis, but also readily co-ordinates to the surface of the quantum dots thus eliminating further nucleation. This is commonly known as capping. Capping groups can further be divided into organic, or inorganic moieties.

Adjusting the electronic and physical properties of the coordinating solvent/ligand has additionally advantages, which can effectively make the quantum dots hydrophobic or hydrophilic, which allows the quantum dots to be 'tailor' made to suit a particular system, e.g. for use in enzymes/proteins studies, or for cross-linking, catalysis etc.

It has been found that quantum dots of ternary I-III-VI$_2$ chalcopyrites having dimensions in the range of 3 to 100 nm, can be made using a ternary SSP according to the present invention. However, it will be understood by persons skilled in the art that careful manipulation of the quantum dot process conditions can yield quantum dots of other sizes. Preferably, quantum dots made from ternary SSPs according to the invention have dimensions in the range of less than 100, preferably 2–60 or 3–30, nm The result is a simple, environmentally sound procedure of manufacturing ternary semiconducting quantum dots. This is highly desirable because quantum dot-based solar cells have been shown in theoretical studies to have a potential efficiency of 66% which is approximately double that of the current state-of-the-art. A key to investigating the possibility of studying and manufacturing highly efficient QD based solar cells is a reproducible synthetic process.

By the present invention, the single source precursor can be prepared as described in detail above, having the correct atomic stoichiometry "built-in." Ternary quantum dots are then synthesized by the following preferred procedure. The ternary SSP according to the invention is dissolved in trioctylphosphine (TOP) under an inert atmosphere. This is subsequently injected into a hot stirred solution of trioctylphosphine oxide in order to facilitate controlled pyrolysis decomposition of the ternary precursor to afford the desired capped ternary quantum dots. In a preferred embodiment, the temperature of the hot stirred solution is less than about 500, preferably less than 400, degrees Celsius. Aliquots of the solution are removed during the formation of the quantum dots and are monitored via UV/VIS spectroscopy, which provides information on their magnitude. When the desired size of the quantum dots is reached, the reaction is then cooled and methanol is added to remove excess reagents, to afford the TOPO-capped ternary nanocrystals (M'M"E$_2$ as described above).

For example the preparation of the CuInS$_2$ quantum dots has been carried out as follows: [{PPh$_3$}$_2$Cu(SEt)$_2$In(SEt)$_2$] (1.945 g, 2.0 mmol) was dissolved in Dioctyl phthalate (10 mL). At approximately 150° C. the precursor dissolved to form a transparent yellow solution; no further change was observed with time at this temperature. At 150° C., the precursor remains, for the most part, intact. Upon increase of the temperature to 200° C. a red powder began to precipitate within a few minutes; a reaction time of 2 h was employed to complete the precipitation and maximize the yield. After cooling to room temperature under argon, toluene (40 mL) was added to the reaction mixture to lower the viscosity of the reaction mixture and the red powder was isolated by centrifugation. The powder was consecutively washed with toluene and methanol to remove reaction byproducts and unreacted starting material and was dried under vacuum at 60° C. The washing and centrifugation steps were carried out in ambient atmosphere. The product appeared only slightly air-sensitive at room temperature; a green tinge was observed on the surface of the powder after several weeks in ambient laboratory atmosphere. Then 0.427 g of this powder was collected and stored in a glovebox. A portion of the powder (100 mg) was placed in a flask containing fresh dioctyl phthalate (10 mL), heated to higher temperatures, 250 or 300° C., and held for 1 h. When the temperature was 250° C., a brown/black powder ("A") was obtained; at 300° C. the resulting powder was black ("B"). Each powder of these powders "A" and "B" was washed and dried in the same manner before analysis. Subsequently, both "A" and "B" were identified as nanocrystalline CuInS$_2$ by XRD.

In a similar procedure as above, quantum dots of CuInSe$_2$ were prepared using the SSP [{PPh$_3$}$_2$Cu(SePh)$_2$In(SePh)$_2$], but the precursor dissolved in the dioctyl phthalate at 138° C. (PPh$_3$)$_2$CuIn(SePh)$_4$ (1.951 g, 1.47 mmol) was dissolved in 10 mL of dioctyl phthalate. A red powder (0.523 g,) was collected after 2 h of heating at 200° C. When needed the reaction was extended to higher temperatures of 250, 300, 350 and 400 to consume all the SSP.

In experiments the resulting quantum dots had an average diameter of nanometer sized dimensions, as determined by laser light scattering. Powder x-ray diffraction on this resulting material confirmed that they corresponded to the chalcopyrite structure of CIS as compared with the JCPS database patterns. UV/VIS studies also have demonstrated that the ternary semiconducting quantum dots can be produced in various magnitudes as can be see by a shift in their optical transmission (cm$^{-1}$).

Although the above-described embodiments constitute the preferred embodiments, it will be understood that various changes or modifications can be made thereto without departing from the spirit and the scope of the present invention as set forth in the appended claims.

What is claimed is:

1. A single source precursor for the deposition of ternary chalcopyrite materials, said single source precursor having a structural formula selected from the group consisting of

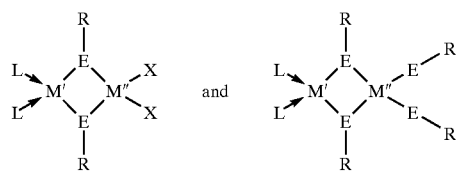

and wherein L is a Lewis base that is coordinated to M' via a dative bond, M' is a Group I-B atom, M" is a Group III-A atom, E is a Group VI-A atom, X is a Group VII-A atom, and each R is individually selected from the group consisting of alkyl, aryl, vinyl, perfluoro alkyl, perfluoro aryl, silane, and carbamato groups, said single source precursor excluding

[{P(C$_6$H$_5$)$_3$}$_2$Cu(S—C$_2$H$_5$)$_2$In(S—C$_2$H$_5$)$_2$],
[{P(C$_6$H$_5$)$_3$}$_2$Cu(Se—C$_2$H$_5$)$_2$In(Se—C$_2$H$_5$)$_2$],
[{P(C$_6$H$_5$)$_3$}$_2$Cu(S(i-C$_4$H$_9$)$_2$In(S(i-C$_4$H$_9$)$_2$],
[{P(C$_6$H$_5$)$_3$}$_2$Cu(Se(i-C$_4$H$_9$)$_2$In(Se(i-C$_4$H$_9$)$_2$],
[{P(C$_6$H$_5$)$_3$}$_2$Ag(Cl)(SC{O}CH$_3$)In(SC{O}CH$_3$)$_2$],
[{P(C$_6$H$_5$)$_3$}$_2$Ag(Cl)(SC{O}C$_6$H$_5$)In(SC{O}C$_6$H$_5$)$_2$],
[{P(C$_6$H$_5$)$_3$}$_2$Ag(SC{O}CH$_3$)$_2$In(SC{O}CH$_3$)$_2$],
[{P(C$_6$H$_5$)$_3$}$_2$Ag(SC{O}C$_6$H$_5$)$_2$In(SC{O}C$_6$H$_5$)$_2$],
[{P(C$_6$H$_5$)$_3$}$_2$Cu(SC{O}C$_6$H$_5$)$_2$In(SC{O}C$_6$H$_5$)$_2$],
[{P(C$_6$H$_5$)$_3$}$_2$Cu(SC{O}C$_6$H$_5$)$_2$Ga(SC{O}C$_6$H$_5$)$_2$],
[{P(C$_6$H$_5$)$_3$}$_2$Ag(SC{O}C$_6$H$_5$)$_2$Ga(SC{O}C$_6$H$_5$)$_2$], and
[{P(C$_6$H$_5$)$_3$}$_2$Ag(SC{O}CH$_3$)$_2$Ga(SC{O}CH$_3$)$_2$].

2. A single source precursor according to claim 1, said singles source precursor being a liquid at room temperature.

3. A single source precursor according to claim 2, said single source precursor being soluble in polar organic solvents and in non-polar organic solvents.

4. A single source precursor according to claim 1, of the formula [{P(n-C$_4$H$_9$)$_3$}$_2$Cu(Se—C$_6$H$_5$)$_2$In(Se—C$_6$H$_5$)$_2$].

5. A single source precursor according to claim 1, of the formula [{P(n-C$_4$H$_9$)$_3$}$_2$Ag(S—C$_2$H$_5$)$_2$In(S—C$_2$H$_5$)$_2$].

6. A single source precursor according to claim 1, of the formula [{P(n-C$_4$H$_9$)$_3$}$_2$Cu(S—C$_2$H$_5$)$_2$In(S—C$_2$H$_5$)$_2$].

7. A single source precursor according to claim 1, of the formula [{P(n-C$_4$H$_9$)$_3$}$_2$Cu(S—C$_3$H$_7$)$_2$In(S—C$_3$H$_7$)$_2$].

8. A single source precursor according to claim 1, of the formula [{P(C$_6$H$_5$)$_3$}$_2$Ag(S—CH$_3$)$_2$In(S—CH$_3$)$_2$].

9. A single source precursor according to claim 1, said single source precursor being effective to yield a I-III-VI$_2$ ternary chalcopyrite material upon heating or pyrolysis of said single source precursor at a temperature less than about 500° C.

10. A single source precursor according to claim 1, said single source precursor being effective to yield a ternary chalcopyrite material having a band gap of about 1.5 eV between a conduction band and a valence band thereof.

11. A single source precursor according to claim 10, said ternary chalcopyrite material being CuInS$_2$.

12. A single source precursor according to claim 1, said single source precursor being effective to yield a ternary chalcopyrite material having a band gap of about 2 eV between a conduction band and a valence band thereof.

13. A single source precursor according to claim 12, said ternary chalcopyrite material being CuGaS$_2$.

14. A single source precursor according to claim 1, said single source precursor being effective to yield a ternary chalcopyrite material having a band gap of 1.5–2 eV between a conduction band and a valence band thereof, said ternary chalcopyrite material being Cu(In:Ga)(S:Se)$_2$.

15. A single source precursor for the deposition of ternary chalcopyrite materials, said single source precursor having a structural formula selected from the group consisting of

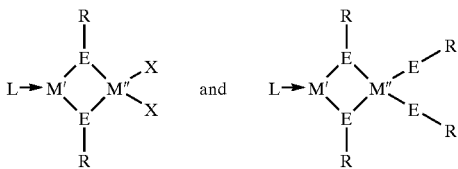

wherein L is a Lewis base that is coordinated to M' via a dative bond, M' is a Group I-B atom, M" is a Group III-A atom, E is a Group VI-A atom, X is a Group VII-A atom, and each R is individually selected from the group consisting of alkyl, aryl, vinyl, perfluoro alkyl, perfluoro aryl, silane, and carbamato groups.

16. A single source precursor according to claim 15, said single source precursor being effective to yield a I-III-VI$_2$ ternary chalcopyrite material upon heating or pyrolysis of said single source precursor at a temperature less than about 500° C.

17. A single source precursor according to claim 15, said single source precursor being effective to yield a ternary chalcopyrite material having a band gap of about 1.5 eV between a conduction band and a valence band thereof.

18. A single source precursor according to claim 17, said ternary chalcopyrite material being CuInS$_2$.

19. A single source precursor according to claim 15, said single source precursor being effective to yield a ternary chalcopyrite material having a band gap of about 2 eV between a conduction band and a valence band thereof.

20. A single source precursor according to claim 19, said ternary chalcopyrite material being CuGaS$_2$.

21. A single source precursor according to claim 15, said single source precursor being effective to yield a ternary chalcopyrite material having a band gap of 1.5–2 eV between a conduction band and a valence band thereof, said ternary chalcopyrite material being Cu(In:Ga)(S:Se)$_2$.

22. A single source precursor for the deposition of ternary chalcopyrite materials, said single source precursor having a structural formula selected from the group consisting of

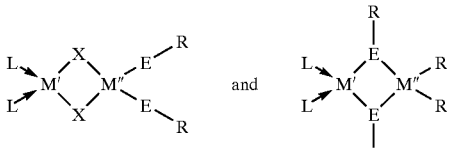

wherein L is a Lewis base that is coordinated to M' via a dative bond, M' is a Group I-B atom, M" is a Group III-A atom, E is a Group VI-A atom, X is a Group VII-A atom, and each R is individually selected from the soup consisting of alkyl, aryl, vinyl, perfluoro alkyl, perfluoro aryl, silane, and carbamato groups.

23. A single source precursor according to claim 22, said single source precursor being effective to yield a I-III-VI$_2$ ternary chalcopyrite material upon heating or pyrolysis of said single source precursor at a temperature less than about 500° C.

24. A single source precursor according to claim 22, said single source precursor being effective to yield a ternary chalcopyrite material having a band gap of about 1.5 eV between a conduction band and a valence band thereof.

25. A single source precursor according to claim 24, said ternary chalcopyrite material being CuInS$_2$.

26. A single source precursor according to claim 22, said single source precursor being effective to yield a ternary chalcopyrite material having a band gap of about 2 eV between a conduction band and a valence band thereof.

27. A single source precursor according to claim 26, said ternary chalcopyrite material being CuGaS$_2$.

28. A single source precursor according to claim 22, said single source precursor being effective to yield a ternary chalcopyrite material having a band gap of 1.5–2 eV between a conduction band and a valence band thereof, said ternary chalcopyrite material being Cu(In:Ga)(S:Se)$_2$.

29. A single source precursor for the deposition of ternary chalcopyrite materials, said single source precursor having a structural formula selected from the group consisting of

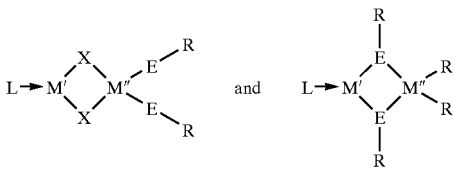

wherein L is a Lewis base that is coordinated to M' via a dative bond, M' is a Group I-B atom, M" is a Group III-A atom, E is a Group VI-A atom, X is a Group VII-A atom, and each R is individually selected from the group consisting of alkyl, aryl, vinyl, perfluoro alkyl, perfluoro aryl, silane, and carbamato groups.

30. A single source precursor according to claim 29, said single source precursor being effective to yield a I-III-VI$_2$ ternary chalcopyrite material upon heating or pyrolysis of said single source precursor at a temperature less than about 500° C.

31. A single source precursor according to claim 29, said single source precursor being effective to yield a ternary chalcopyrite material having a band gap of about 1.5 eV between a conduction band and a valence band thereof.

32. A single source precursor according to claim 31, said ternary chalcopyrite material being CuInS$_2$.

33. A single source precursor according to claim 29, said single source precursor being effective to yield a ternary chalcopyrite material having a band gap of about 2–2.4 eV between a conduction band and a valence band thereof.

34. A single source precursor according to claim 33, said ternary chalcopyrite material being CuGaS$_2$.

35. A single source precursor according to claim 29, said single source precursor being effective to yield a ternary chalcopyrite material having a band gap of 1.5–2 eV between a conduction band and a valence band thereof, said ternary chalcopyrite material being Cu(In:Ga)(S: Se)$_2$.

36. A single source precursor for the deposition of ternary chalcopyrite materials, said single source precursor having the empirical formula [{L}$_n$M'(ER)$_x$(X)$_y$(R)$_z$M"], wherein x is 3, x+y+z=4, n is greater than or equal to 1, L is a Lewis base that is coordinated to M' via a dative bond, M' is a Group I-B atom, M" is a Group III-A atom, E is a Group VI-A atom, X is a Group VII-A atom, and each R is individually selected from the group consisting of alky, aryl, vinyl, perfluoro alkyl, perfluoro aryl, silane, and carbamato groups, said single source precursor excluding
[{P(C$_6$H$_5$)$_3$}$_2$Cu (S—C$_2$H$_5$)$_2$In(S—C$_2$H$_5$)$_2$],
[{P(C$_6$H$_5$)$_3$}$_2$Cu (Se—C$_2$H$_5$)$_2$In(Se—C$_2$H$_5$)$_2$],
[{P(C$_6$H$_5$)$_3$}$_2$Cu (S(i-C$_4$H$_9$))$_2$In(S(i-C$_4$H$_9$))$_2$],

[{P(C₆H₅)₃}₂Cu (Se(i-C₄H₉))₂In(Se(i-C₄H₉))₂],
[{P(C₆H₅)₃}₂Ag(Cl)(SC{O}CH₃)In(SC{O}CH₃)₂],
[{P(C₆H₅)₃}₂Ag(Cl)(SC{O}C₆H₅)In(SC{O}C₆H₅)₂],
[{P(C₆H₅)₃}₂Ag(SC{O}CH₃)₂In(SC{O}CH₃)₂],
[{P(C₆H₅)₃}₂Ag(SC{O}C₆H₅)₂In(SC{O}C₆H₅)₂],
[{P(C₆H₅)₃}₂Cu(SC{O}C₆H₅)₂In(SC{O}C₆H₅)₂],
[{P(C₆H₅)₃}₂Cu(SC{O}C₆H₅)₂Ga(SC{O}C₆H₅)₂],
[{P(C₆H₅)₃}₂Ag(SC{O}C₆H₅)₂Ga(SC{O}C₆H₅)₂], and
[{P(C₆H₅)₃}₂Ag(SC{O}CH₃)₂Ga(SC{O}CH₃)₂].

37. A single source precursor for the deposition of ternary chalcopyrite materials, said single source precursor being a liquid at room temperature and being effective to yield a ternary chalcopyrite material upon heating or pyrolysis thereof.

38. A single source precursor according to claim 37, said single source precursor being effective to yield a I-III-VI₂ ternary chalcopyrite material upon heating or pyrolysis of said single source precursor at a temperature less than about 500° C.

39. A method of depositing ternary chalcopyrite materials comprising the steps of:

a) providing a first single source precursor for said ternary chalcopyrite material, said first single source precursor having the empirical formula [{L}$_n$M'(ER)$_x$(X)$_y$(R)$_z$M''], wherein x is 1–4, x+y+z=4, n is greater than or equal to 1, L is a Lewis base that is coordinated to M' via a dative bond, M' is a Group I-B atom, M'' is a Group III-A atom, E is a Group VI-A atom, X is a Group VII-A atom, and each R is individually selected from the group consisting of alkyl, aryl, vinyl, perfluoro alkyl, perfluoro aryl, silane, and carbamato groups, said single source precursor excluding

[{P(C₆H₅)₃}₂Cu(S—C₂H₅)₂In(S—C₂H₅)₂],
[{P(C₆H₅)₃}₂Cu(SC{O}C₆H₅)₂In(SC{O}C₆H₅)₂],
[{P(C₆H₅)₃}₂Cu(SC{O}C₆H₅)₂Ga(SC{O}C₆H₅)₂],
[{P(C₆H₅)₃}₂Ag(SC{O}C₆H₅)₂In(SC{O}C₆H₅)₂],
[{P(C₆H₅)₃}₂Ag(SC{O}C₆H₅)₂Ga(SC{O}C₆H₅)₂],
[{P(C₆H₅)₃}₂Ag(SC{O}CH₃)₂In(SC{O}CH₃)₂], and
[{P(C₆H₅)₃}₂Ag(SC{O}CH₃)₂Ga(SC{O}CH₃)₂];
and b) depositing the single source precursor on a substrate using a spray CVD technique.

40. A method according to claim 39, said single source precursor having a structural formula selected from the group consisting of

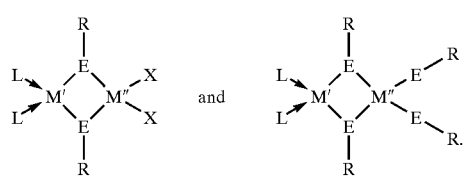

41. A method according to claim 39, said single source precursor having a structural formula selected from the group consisting of 42. A method according to claim 39, said single source precursor having a structural formula selected from the group consisting of

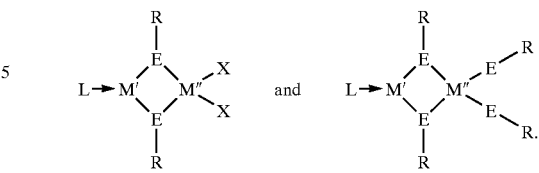

43. A method according to claim 39, said single source precursor having a structural formula selected from the group consisting of

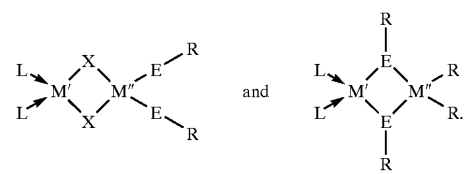

44. A method according to claim 39, said single source precursor having three E-R groups.

45. A method according to claim 39, comprising the steps of providing a second single source precursor, and applying said first and second single source precursors on said substrate via said spray CVD technique.

46. A method of making a single source precursor for the deposition of ternary chalcopyrite materials comprising the step of carrying out the following reaction:

4M$_{ALK}$ER+M'X₃+M''X+nL→[{L}$_n$M'(ER)₂M''(ER)₂]

wherein

M$_{ALK}$ is an alkali metal element,

E is a Group VI-A element,

R is selected from the group consisting of alkyl, aryl, vinyl, perfluoro alkyl, perfluoro aryl, silane and carbamato groups, M' is a Group I-B element, M'' is a Group III-A element, X is a Group VII-A element, and n is greater than or equal to 1.

47. A method according to claim 46, wherein said single source precursor is made in a single step consisting essentially of said reaction.

48. A method according to claim 46, wherein the ionic complex [L$_{(n)}$M''(CH₃CN)$_{(4-n)}$]⁺ is formed in situ as said reaction proceeds.

49. A method according to claim 46, said reaction being carried out under anaerobic conditions.

50. A method according to claim 46, said reaction being carried out under non-anaerobic conditions.

51. A method of making a quantum dot comprising the steps of:
   a) providing a single source precursor for a ternary chalcopyrite material; and
   b) pyrolyzing said single source precursor to yield a quantum dot made of ternary chalcopyrite material having dimensions less than 100 nanometers.

52. A method according to claim 51, said quantum dot made of a ternary I-III-VI$_2$ chalcopyrite material.

53. A method according to claim 51, said quantum dot made of a ternary I-III$_5$-VI$_8$ chalcopyrite material.

54. A method according to claim 51, said pyrolyzing step being carried out at a temperature less than about 500° C.

55. A method according to claim 51, said single source precursor having the empirical formula [{L}$_n$M'(ER)$_x$(X)$_y$(R)$_z$M"], wherein x is 1–4, x+y+z=4, n is greater than or equal to 1, L is a Lewis base that is coordinated to M' via a dative bond, M' is a Group I-B atom, M" is a Group III-A atom, E is a Group VI-A atom, X is a Group VII-A atom, and each R is individually selected from the group consisting of alkyl, aryl, vinyl, perfluoro alkyl, perfluoro aryl, silane, and carbamato groups.

56. A single source precursor according to claim 1, said single source precursor being effective to yield a I-III$_5$-VI$_8$ ternary chalcopyrite material upon heating or pyrolysis of said single source precursor.

57. A single source precursor according to claim 29, said single source precursor being effective to yield a ternary chalcopyrite material having a band gap of 0.5–3.5 eV between a conduction band and a valence band thereof, said ternary chalcopyrite material being (Cu:Ag:Au)$_1$(Al:In:Ga)$_1$(S:Se:Te)$_2$.

58. A single source precursor according to claim 1, said Group VI-A atom being selected from the group consisting of S, Se and Te.

59. A single source precursor according to claim 15, said Group VI-A atom being selected from the group consisting of S, Se and Te.

* * * * *

UNITED STATES PATENT AND TRADEMARK OFFICE
CERTIFICATE OF CORRECTION

PATENT NO. : 6,992,202 B1
APPLICATION NO. : 10/698118
DATED : January 31, 2006
INVENTOR(S) : Kulbinder K. Banger et al.

It is certified that error appears in the above-identified patent and that said Letters Patent is hereby corrected as shown below:

Column 20:

Line 10, after "$Cu(S(i-C_4H_9)$" and before "$_2$", please insert --)--.
Line 10, after "$In(S(i-C_4H_9)$" and before "$_2$", please insert --)--.
Line 11, after "$Cu(Se(i-C_4H_9)$" and before "$_2$", please insert --)--.
Line 11, after "$In(Se(i-C_4H_9)$" and before "$_2$", please insert --)--.

Claim 22

Line 17, please delete "soup" and insert therefor --group--.

Claim 35

Line 5, please delete "(S: Se)" and insert therefore --(S:Se)--.

Claim 36

Line 8, please delete "alky" and insert therefor --alkyl--.
Line 11, after "Cu" and before "(", please delete the space.
Line 12, after "Cu" and before "(", please delete the space.
Line 13, after "Cu" and before "(", please delete the space.
Line 14, after "Cu" and before "(", please delete the space.

UNITED STATES PATENT AND TRADEMARK OFFICE
CERTIFICATE OF CORRECTION

PATENT NO. : 6,992,202 B1
APPLICATION NO. : 10/698118
DATED : January 31, 2006
INVENTOR(S) : Kulbinder K. Banger et al.

It is certified that error appears in the above-identified patent and that said Letters Patent is hereby corrected as shown below:

Claim 43

Line 6, please delete " 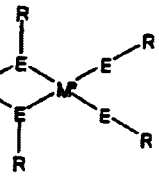 " and insert therefore

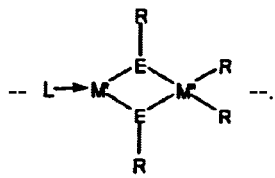 --.

Signed and Sealed this

Twenty-fourth Day of October, 2006

JON W. DUDAS
*Director of the United States Patent and Trademark Office*